(12) United States Patent
Takakura et al.

(10) Patent No.: US 6,358,726 B1
(45) Date of Patent: Mar. 19, 2002

(54) THERMOSTABLE PROTEASE

(75) Inventors: Hikaru Takakura; Mio Morishita, both of Otsu; Tomoko Shimojo, Kyoto; Kiyozo Asada, Shiga; Ikunoshin Kato, Uji, all of (JP)

(73) Assignee: Takara Shuzo Co., Ltd., Kyoto (JP)

(*) Notice: Subject to any disclaimer, the term of this patent is extended or adjusted under 35 U.S.C. 154(b) by 0 days.

(21) Appl. No.: 09/445,472

(22) PCT Filed: Jun. 4, 1998

(86) PCT No.: PCT/JP98/02465

§ 371 Date: Dec. 8, 1999

§ 102(e) Date: Dec. 8, 1999

(87) PCT Pub. No.: WO98/56926

PCT Pub. Date: Dec. 17, 1998

(30) Foreign Application Priority Data

Jun. 10, 1997 (JP) .............................................. 9-151969

(51) Int. Cl.[7] .................................................. C12N 9/50
(52) U.S. Cl. ........................ 435/219; 435/220; 435/212
(58) Field of Search ................................ 435/183, 195, 435/219, 220, 243, 252.1; 530/350

(56) References Cited

U.S. PATENT DOCUMENTS 5,756,339 A  5/1998  Mitta et al. .................. 435/220

OTHER PUBLICATIONS

Stahl et al., "Replacement of the *Bacillus substilis* Subtilisin Structural Gene with an In Vitro–Derived Deletion Mutation", *Journal of Bacteriology*, 152:411–418 (May 1984).

Yoshimoto et al., "Cloning and Expression of Subtilisin Amylosacchariticus Gene", *J. Biochem.*, 103:1060–1065 (1988).

Nakamura et al., "Nucleotide Sequence of the Subtilisin NAT Gene, apr N, of Bacillus subtilis (natto)", *Biosci. Biotech. Biochem*, 56:1869–1871 (1992).

Asada et al. Accession AAR87009. Hyperthermostable protease. May 10, 1996 (Aligment No. 3).*

* cited by examiner

*Primary Examiner*—Nashaat T. Nashed
*Assistant Examiner*—Christopher L. Fronda
(74) *Attorney, Agent, or Firm*—Browdy and Neimark

(57) ABSTRACT

A hyperthermostable protease having the amino acid sequence represented by the SEQ ID NO:1 of the Sequence Listing or a sequence derived therefrom by deletion, substitution, insertion or addition of one to several amino acid residues, a gene encoding the hyperthermostable protease, and a process for preparing the protease, aiming at providing by genetic engineering techniques a hyperthermophile protease which is advantageous for industrial use.

2 Claims, 7 Drawing Sheets

Fig. 2

```
                   10          20          30          40          50
PFUL         MNKKGLTVLF  IAIMLLSVVP  VHFVSAETPP  VSSENSTTSI  LPNQQVVTKE
TCES                                 MKRLGAVV    LALVLVGLLA  VVRNNAVQQK
subtilisin                                       GTALAAPVKP  MRGKKVWISL 60          70          80          90         100
PFUL         VSQAALNAIM  KGQPNMVLII  KTKEGKLEEA  KTELEKLGAE  ILDENRVLNM
TCES         NYGLLTPGLF  KKVQRMNWNQ  EVDTVIMFGS  YGDRDRAVKV  LRLMGAQVKY
subtilisin   LFALALIFTM  AFGSTSSAQA  AGKSNGEKKY  IVGFKQTMST  MSAAKKKDVI 110         120         130         140         150
PFUL         LLVKIKPEKV  KELNYISSLE  KAWLNREVKL  SPPIVEKDVK  TKEPSLEPKM
TCES         SYKIIPAVAV  KIKARDLLLI  AGMIDTGYFG  NTRVSGIKFI  QEDYKVQVDD
subtilisin   SEKGGKVQKQ  FKYVDAASAT  LNEKAVKELK  KDPSVAYVEE  DHVAHAYAQS 160         170         180         190         200
PFUL         YNSTWVINAL  QFIQEFGYDG  SGVVVAVLDT  GVDPNHPFLS  ITPDGRRKII
TCES         ATSVSQIGAD  TVWNSLGYDG  SGVVVAIVDT  GIDANHPDLK  GKVIGWYDAV
subtilisin   VPYGVSQIKA  PALHSQGYTG  SNVKVAVIDS  GIDSSHPDLK  VAGGASMVPS 210         220         230         240         250
PFUL         EWKDFTDEGF  VDTSFSFSKV  VNGTLIINTT  FQVASGLTLN  ESTGLMEYVV
TCES         NGRSTPYDDQ  ----------  ----------  ----------  ----------
subtilisin   ETNPFQDNN-  ----------  ----------  ----------  ----------

260         270         280         290         300
PFUL         KTVYVSNVTI  GNITSANGIY  HFGLLPERYF  DLNFDGDQED  FYPVLLVNST
TCES         ----------  ----------  ----------  ----------  ----------
subtilisin   ----------  ----------  ----------  ----------  ----------
```

Fig. 3

```
                  310        320        330        340        350
PFUL       GNGYDIAYVD TDLDYDFTDE VPLGQYNVTY DVAVFSYYYG PLNYVLAEID
TCES       ---------- ---------- ---------- ---------- ----------
subtilisin ---------- ---------- ---------- ---------- ----------

360        370        380        390        400
PFUL       PNGEYAVFGW DGHGHGTHVA GTVAGYDSNN DAWDWLSMYS GEWEVFSRLY
TCES       ---------- --GHGTHVA- GIVAGTGSVN SQ-------- ----------
subtilisin ---------- ---SHGTHVA GTVAA--LNN SI-------- ----------

410        420        430        440        450
PFUL       GWDYTNVTTD TVQGVAPCAQ IMAIRVLRSD GRGSMWDIIE CMTYAATHGA
TCES       ---------- -YIGVAPGAK LVGVKVLGAD GSGSVSTIIA CVDWVQNKD-
subtilisin ---------- GVLGVAPSAS LYAVKVLGAD GSCQYSWIIN CIEWAIANNM 460        470        480        490        500
PFUL       ----DVISMS LGGNAPYLDG TDPESVAVDE LTEKYGVVFV IAAGNEGPGI
TCES       KYGIRVINLS LGSSQSS-DC TDSLSQAVNN AWDA-GIVVC VAAGNSGPNT
subtilisin ----DVINMS LGGP-----SG SAALKAAVDK AVAS-GVVVV AAAGNEGTSG 510        520        530        540        550
PFUL       N--IVGSPGV ATKAITVGAA AVPINVGVYV SQALGYPDYY GFYYFPAYTN
TCES       Y--TVGSPAA ASKVITVGAV DSNDN----- ---------- ----------
subtilisin SSSTVGYPGK YPSVIAVGAV DSSNQ----- ---------- ----------

560        570        580        590        600
PFUL       VRIAFFSSRG PRIDGEIKEN VVAPGYGIYS SLPMWIGGAD F------MS
TCES       --IASFSSRG PTADGRLKPE VVAPGVDIIA PRASGTSMGT PINDYYTKAS
subtilisin ---RASFSSVG PELD------ VMAPGVSIQS TLPGNKYGA- ----------YN
```

Fig. 4

```
                    610              620              630              640              650
PFUL       GTSMATPHVS       GVVALLISGA       KAEGIYYNPD       IIKKVLESGA       TWLEGDPYTG
TCES       GTSMATPHVS       GVAALILQAH       PSWTPDKVKT       ----ALIETA       DIVAPKEIAD
subtilisin GTSMASPHVA       GAAALILSKH       PNWTNTQVRS       ----SLENTT       TKL-GES---

660              670              680              690              700
PFUL       QKYTELDQGH       GLVNVTKSWE       ILKAINGTTL       PIVDHWADKS       YSDFAEYLGV
TCES       ----IAYGA        GRVNVYKAIK       YDDYAKLTFT       GSVADKGSAT       HTFDVSGATF
subtilisin ----FYYGK        GLINVQAAAQ       *

710              720              730              740              750
PFUL       DVIRGLYARN       SIPDIVEWHI       KYVGDTEYRT       FEIYATEPWI       KPFVSGSVIL
TCES       VTATLYWDTG       SSDIDLYLYD       PNGNEVDYSY       TAYYGFEKVG       YYNPTAGTWT 760              770              780              790              800
PFUL       ENNTEFVLRV       KYDVEGLEPG       LYVGRIIIDD       PTTPVIEDEI       LNTIVIPEKF
TCES       VKVVSYKGAA       NYQVDVVSDG       SLSQSGGGNP       NPNPNPNPTP       TTDTQTFFTGS 810              820              830              840              850
PFUL       TPENNYTLTW       YDINGPEMVT       HHFFTVPEGV       DVLYAMTTYW       DYGLYRPDGM
TCES       VNDYWDTSDT       FTMNVNSGAT       KITGDLTFDT       SYNDLDLYLY       DPNGNLVDRS 860              870              880              890              900
PFUL       FVFPYQLDYL       PAAVSNPMPG       NWELVWTGFN       FAPLYESGFL       VRIYGVEITP
TCES       TSSNSYEHVE       YANPAPGTWT       FLVYAYRTYG       WADYQLKAVV       YYG*

910              920              930              940              950
PFUL       SVWYINRTYL       DTNTEFSIEF       NITNIYAPIN       ATLIPIGLGT       YNASVESVGD
```

Fig. 5

```
PFUL            960        970        980        990       1000
        GEFFIKGIEV PEGTAELKIR IGNPSVPNSD LDLYLYDSKG NLVALDGNPT

PFUL           1010       1020       1030       1040       1050
        AEEEVVVEYP KPGVYSIVVH GYSVRDENGN PTTTTFDLVV QMTLDNGNIK

PFUL           1060       1070       1080       1090       1100
        LDKDSIILGS NESVVVTANI TIDRDHPTGV YSGIIEIRDN EVYQDTNTSI

PFUL           1110       1120       1130       1140       1150
        AKIPITLVID KADFAVGLTP AEGVLGEARN YTLIVKHALT LEPVPNATVI

PFUL           1160       1170       1180       1190       1200
        IGNYTYLTDE NGTVTFTYAP TKLGSDEITV IVKKENFNTL EKTFQITVSE

PFUL           1210       1220       1230       1240       1250
        PEITEEDINE PKLAMSSPEA NATIVSVEME SEGGVKKTVT VEITINGTAN

PFUL           1260       1270       1280       1290       1300
        ETATIVVPVP KKAENIEVSG DHVISYSIEE GEYAKYVIIT VKFASPVTVT

PFUL           1310       1320       1330       1340       1350
        VTYTIYAGPR VSILTLNFLG YSWYRLYSQK FDELYQKALE LGVDNETLAL

PFUL           1360       1370       1380       1390       1400
        ALSYHEKAKE YYEKALELSE GNIIQYLGDI RLLPPLRQAY INEMKAVKIL

PFUL           1410
        EKAIEELEGE E*
```

THERMOSTABLE PROTEASE

The present application is the national stage under 35 U.S.C. 371 of PCT/JP98/02465, filed Jun. 4, 1998, which claims priority from JP 151969/1997, filed Jun. 10, 1997.

TECHNICAL FIELD

The present invention relates to a hyperthermostable protease useful as an enzyme for industrial use, a gene encoding the same and a method of producing the enzyme by genetic engineering technique.

BACKGROUND ART

A protease is an enzyme that cleaves peptide bonds in proteins. A number of such enzymes have been found in animals, plants and microorganisms. The protease is used as a reagent for laboratory use and as a pharmaceutical, as well as in industrial fields, for example, as an additive for a detergent, for processing foods and for chemical synthesis utilizing a reverse reaction. Therefore, it can be said that the protease is an extremely important enzyme for industries. Since high physical and chemical stability is required for a protease used in industrial fields, a thermostable enzyme is preferably used among others. Since proteases produced by bacteria of genus Bacillus exhibit relatively high thermostability, they are mainly used as proteases for industrial use. However, in search of a more superior enzyme, attempts have been made to obtain an enzyme from a microorganism growing at high temperature, for example, a thermophilic bacterium of genus Bacillus or a hyperthermophile.

For example, a hyperthermophile *Pyrococcus furiosus* is known to produce a protease (Appl. Environ. Microbiol., 56:1992–1998 (1990); FEMS Microbiol. Letters, 71:17–20 (1990); J. Gen. Microbiol., 137:1193–1199 (1991)).

In addition, a hyperthermophile, Pyrococcus sp. strain KOD1, is reported to produce a thiol protease (a cysteine protease) (Appl. Environ. Microbiol., 60:4559–4566 (1994)). Hyperthermophiles of genus Thermococcus, genus Staphylothermus and genus Thermobacteroides are also known to produce proteases (Appl. Microbiol. Biotechnol., 34:715–719 (1991)).

The proteases from the hyperthermophiles as described above have high thermostability. Therefore, it is expected that they may be used in place of the thermostable proteases currently in use or in a field in which use of a protease has not been considered.

However, most of the microorganisms producing these enzymes grow only at high temperature. For example, *Pyrococcus furiosus* needs to be cultured at 90–100° C. Culturing at such high temperature is disadvantageous in view of energy cost. Furthermore, the productivities of the proteases from the hyperthermophiles are lower than the productivities of the conventional microbial proteases. Thus, the methods for industrially producing the proteases from the hyperthermophiles have problems.

By the way, production of an enzyme by genetic engineering technique by isolating the gene for the enzyme of interest and introducing it into a host microorganism that can readily be cultured is currently common in the art. However, the gene for the enzyme introduced into the host is not always expressed so efficiently as expected. It is believed that the main cause is that the GC content or the codon usage of the introduced gene is different from those of the genes of the host. Therefore, it is necessary to optimize the expression method for each gene to be introduced and/or each host in order to accomplish a suitable productivity of an enzyme for the intended use.

OBJECTS OF THE INVENTION

The objects of the present invention are to provide a protease from a hyperthermophile which is advantageous for industrial use, to isolate a gene encoding the protease from the hyperthermophile, and to provide a method of producing the hyperthermostable protease using the gene by genetic engineering technique in order to solve the problems as described above.

SUMMARY OF THE INVENTION

Among proteases produced by hyperthermophiles, some may be classified into the subtilisin-type of alkaline proteases based on the amino acid sequence homology. When a gene for such a protease is introduced into *Bacillus subtilis* which is generally used for production by genetic engineering technique, the productivity of this enzyme is much less than that of a protein inherently produced by *Bacillus subtilis*.

The present inventors have studied intensively and found that, by placing a gene encoding a signal peptide (signal sequence) derived from a subtilisin upstream a protease gene derived from a hyperthermophile to be expressed, and modifying the amino acid sequence around the cleavage site, the gene of interest is expressed in *Bacillus subtilis* with high efficiency. Furthermore, it has been found that the expression level of the enzyme can be increased by deleting a portion that is not essential for the enzymatic activity in the protease gene derived from the hyperthermophile of interest. Thus, the present invention has been completed.

The present invention is outlined as follows. The first invention of the present invention is a thermostable protease having an amino acid sequence represented by the SEQ ID NO:1 of the Sequence Listing, and a protease having an amino acid sequence in which one or several amino acid residues are deleted, substituted, inserted or added in the amino acid sequence represented by the SEQ ID NO:1 of the Sequence Listing and having a thermostable protease activity.

The second invention of the present invention is a gene encoding the thermostable protease of the first invention, and a thermostable protease gene that hybridizes with the gene.

The third invention of the present invention is a gene to be used for producing a thermostable protease derived from a hyperthermophile by genetic engineering technique, characterized in that the gene encodes an amino acid sequence represented by formula I:

SIG-Ala-Gly-Gly-Asn-PRO [I] (SEQ ID NO:30)

wherein SIG represents an amino acid sequence of a signal peptide derived from a subtilisin, PRO represents an amino acid sequence of a protein to be expressed. Preferably, SIG is the amino acid sequence represented by the SEQ ID NO:3 of the Sequence Listing. Preferably, PRO is an amino acid sequence of a hyperthermostable protease derived from a hyperthermophile, more preferably, an amino acid sequence of a protease derived from *Pyrococcus furiosus*.

The fourth invention of the present invention relates to a method of producing a protein by genetic engineering technique, characterized in that the method comprises culturing a bacterium of genus Bacillus into which the gene of the third invention is introduced, and collecting the protein of interest from the culture.

The fifth invention of the present invention is a plasmid used for producing a protein by genetic engineering technique, characterized in that the gene of the third invention is inserted into the plasmid.

A mutation such as deletion, substitution, insertion or addition of one to several amino acid residues in an amino acid sequence may be generated in a naturally occurring protein including the protein disclosed by the present invention. Such mutation may be generated due to a polymorphism or a mutation of the gene encoding the protein, or due to a modification of the protein in vivo or during purification after synthesis may occur. Nevertheless, it is known that such a mutated protein may exhibit physiological and biological activities equivalent with those of a protein without a mutation. This is applicable to a protein in which such a mutation is introduced into its amino sequence artificially, in which case it is possible to generate a wide variety of mutations. For example, it is known that a polypeptide in which a cysteine residue in the amino acid sequence of human interleukin-2 (IL-2) is substituted with a serine residue retains an interleukin-2 activity (Science, 224:1431 (1984)). Thus, a protease having an amino acid sequence in which one or several amino acid residues are deleted, substituted, inserted or added in the amino acid sequence disclosed by the present invention and having a protease activity equivalent with that of the protease of the present invention is within the scope of the present invention.

As used herein, "a gene which hybridizes (with a particular gene)" is a gene having a base sequence similar to that of the particular gene. It is likely that a gene having a base sequence similar to that of a particular gene encodes a protein having an amino acid sequence and a function similar to those of the protein encoded by the particular gene. Similarity of base sequences of genes can be examined by determining whether or not the genes or portions thereof form a hybrid (hybridize) each other under stringent conditions. By utilizing this procedure, a gene that encodes a protein having a similar function with that of the protein encoded by the particular gene can be obtained. That is, a gene having a similar base sequence with that of the gene of the present invention can be obtained by using the gene obtained by the present invention or a portion thereof as a probe to carry out hybridization according to a known method. Hybridization can be carried out according to the method, for example, as described in T. Maniatis et al. eds., Molecular Cloning: A Laboratory Manual 2nd ed., published by Cold Spring Harbor Laboratory, 1989. More specifically, hybridization can be carried out under the following conditions. Briefly, a membrane onto which DNAs are immobilized is incubated in 6×SSC (1×SSC represents 0.15 M NaCl, 0.015 M sodium citrate, pH 7.0) containing 0.5% SDS, 0.1% bovine serum albumin (BSA), 0.1% polyvinylpyrorridone, 0.1% Ficoll 400, 0.01% denatured salmon sperm DNA at 50° C. for 12–20 hours with a probe. After incubation, the membrane is washed until the signals for the immobilized DNAs can be distinguished from background, starting from washing in 2×SSC containing 0.5% SDS at 37° C. while decreasing the SSC concentration down to 0.1× and raising the temperature up to 50° C.

Alternatively, instead of hybridization, a gene amplification method (e.g., PCR method) which employs portions of the base sequence of the gene obtained by the present invention as primers can be utilized. Whether or not the gene thus obtained encodes a protein having the function of interest can be determined by expressing the gene utilizing a suitable host and a suitable expression system and examining the activity of the resulting protein.

BRIEF DESCRIPTION OF THE DRAWINGS

FIGS. 2–5 compare the amino acid sequences of Protease PFUL (SEQ ID NO:6), Protease TCES (SEQ ID NO:12) and a subtilisin (SEQ ID NO:31).

DETAILED DESCRIPTION OF THE INVENTION

Figure 1:
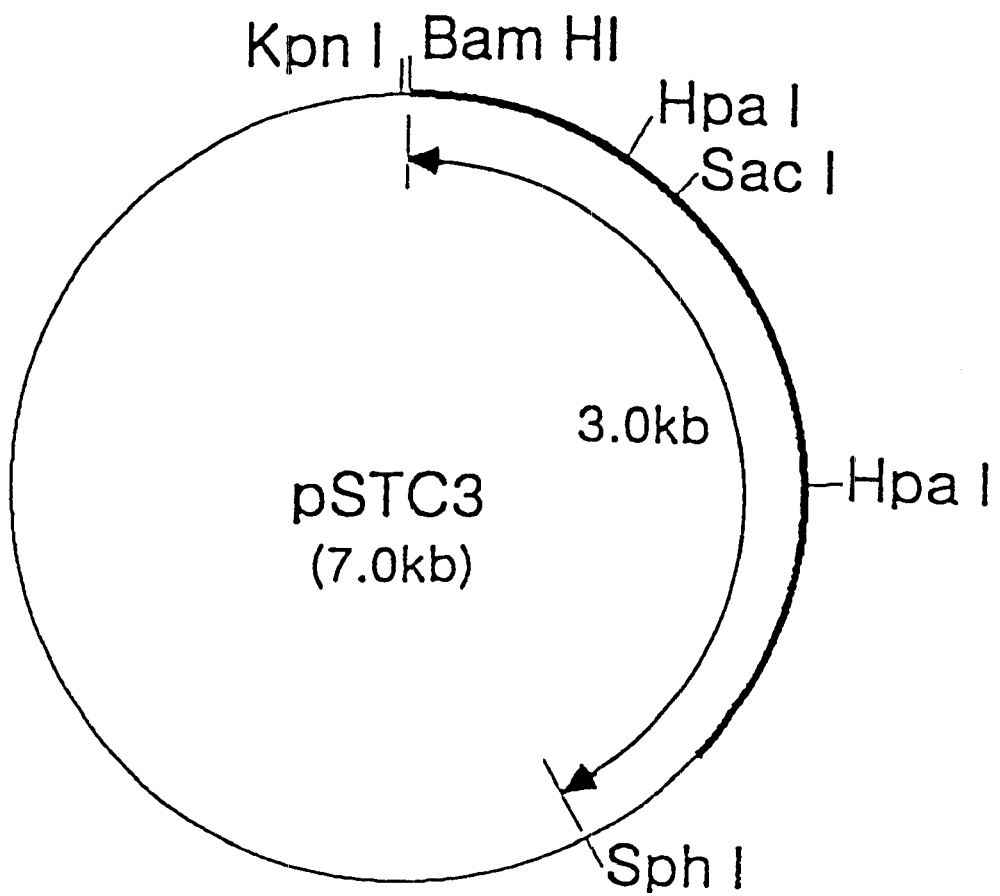
FIG. 1 is the restriction enzyme map of the plasmid pSTC3.

The hyperthermostable protease according to the present invention includes proteases from various hyperthermophiles. For example, WO 95/34645 describes proteases from *Pyrococcus furiosus* and *Thermococcus celer*.

A protease gene from *Pyrococcus furiosus* DSM3638 was isolated from a genomic DNA library of the strain based on the expression of a thermostable protease activity. A plasmid containing this gene is designated as the plasmid pTPR12. *Escherichia coli* JM109 transformed with this plasmid is designated and indicated as *Escherichia coli* JM109/pTPR12, and deposited on May 24, 1994 (the date of the original deposit) under Budapest Treaty at the National Institute of Bioscience and Human-Technology, Agency of Industrial Science and Technology, Ministry of International Trade and Industry, 1–3, Higashi 1-chome, Tsukuba-shi, Ibaraki-ken, Japan under accession number FERM BP-5103.

This protease is designated as Protease PFUL hereinafter. Protease PFUL is a protease having high thermostability and exhibits a protease activity even at 95° C.

The base sequence of the DNA fragment derived from *Pyrococcus furiosus* inserted into the plasmid pTPR12 has been determined. The base sequence of the portion of approximately 4.8 kb bordered by two DraI sites in the DNA fragment inserted into the plasmid pTPR12 is shown in the SEQ ID NO:5 of the Sequence Listing. Furthermore, the amino acid sequence of the gene product deduced from the base sequence is shown in the SEQ ID NO:6 of the Sequence Listing. In other words, the amino acid sequence as shown in the SEQ ID NO:6 of the Sequence Listing is the amino acid sequence of Protease PFUL. As shown in the sequence, Protease PFUL consists of 1398 amino acid residues and is a protease with a high molecular weight of over 150,000.

Comparison of the amino acid sequence of Protease PFUL as shown in SEQ ID NO:6 of the Sequence Listing with known amino acid sequences of proteases from microorganisms has revealed that the amino acid sequence of the first half portion of Protease PFUL is homologous to those of a series of alkaline serine proteases represented by a subtilisin (Protein Engineering, 4:719–737 (1991)), and that there is extremely high homology around the four amino acid residues which are believed to be important for the catalytic activity of the protease.

As described above, it has been found that a region common among proteases derived from mesophiles is conserved in the amino acid sequence of Protease PFUL produced by a hyperthermophile *Pyrococcus furiosus*. Thus, it is expected that a homologous protease produced by a hyperthermophile other than *Pyrococcus furiosus* also has this region.

For example, a gene for a hyperthermostable protease can be screened by performing PCR using a chromosomal DNA from various hyperthermophiles as a template and the oligonucleotides PRO-1F, PRO-2F, PRO-2R and PRO-4R in combination as primers. These oligonucleotides are synthesized based on the base sequence in the Protease PFUL gene which encodes a region exhibiting high homology with subtilisins or the like within the amino acid sequence of Protease PFUL. The base sequences of oligonucleotides PRO-1F, PRO-2F, PRO-2R and PRO-4R are shown in the SEQ ID NOS:7, 8, 9 and 10 of the Sequence Listing, respectively.

As a hyperthermophile from which the protease according to the present invention is derived, a bacterium belonging to genus Pyrococcus, genus Thermococcus, genus Staphylothermus, genus Thermobacteroides and the like can be used. As a bacterium belonging to genus Thermococcus, for example, Thermococcus celer DSM2476 can be used. This strain is available from Deutsche Sammlung von Mikroorganismen und Zellkulturen GmbH. When performing PCR using a chromosomal DNA from Thermococcus celer DSM2476 as a template and a combination of the oligonucleotides PRO-1F and PRO-2R or the oligonucleotide PRO-2F and Pro-4R as primers, specific DNA fragments are amplified, indicating the presence of a protease gene. Furthermore, by creating recombinant plasmids in which the DNA fragments are inserted into an appropriate plasmid vector and determining the base sequences of the inserted DNA fragments by dideoxy method, the amino acid sequences encoded by the fragments can be deduced. As a result, it proved that such DNA fragments encode an amino acid sequence that is homologous to the amino acid sequences of Protease PFUL and alkaline serine proteases from various microorganisms and that the PCR-amplified DNA fragments were amplified from a protease gene as a template.

Next, a gene for a hyperthermostable protease (for example, a gene for a hyperthermostable protease produced by Thermococcus celer) can be obtained by screening a gene library from a hyperthermophile using the PCR-amplified DNA fragment or the oligonucleotide as described above as a probe.

For example, a phage clone containing the gene of interest can be obtained by performing plaque hybridization against a library using the PCR-amplified DNA fragment as a probe. Such library is generated by ligating lambda GEM-11 vector (Promega) and DNA fragments resulting from partial digestion of the chromosomal DNA from Thermococcus celer DSM2476 with a restriction enzyme Sau3AI, then packaging them into lambda phage particles by in vitro packaging method.

It is found that a protease gene exists in a SacI fragment of approximately 1.9 kb by analyzing a DNA fragment contained in a phage clone thus obtained. Furthermore, it is found that this fragment lacks the 5' region of the protease gene by determining its base sequence. The 5' region can be obtained by PCR using a cassette and cassette primers (Takara Shuzo Gene Technology Product Guide, 1994–1995, pp.250–251). Thus, a DNA fragment which covers the 5' region of the hyperthermostable protease gene which is absent in the plasmid pTCS6 can be obtained. Furthermore, the base sequence of the entire hyperthermostable protease gene derived from Thermococcus celer can be determined from the base sequences of the two DNA fragments.

The base sequence of an open reading frame found in the determined base sequence is shown in the SEQ ID NO:11 of the Sequence Listing, and the amino acid sequence deduced from the base sequence is shown in the SEQ ID NO:12 of the Sequence Listing. The base sequence of the gene encoding the hyperthermostable protease from Thermococcus celer and the amino acid sequence of the protease were thus determined. This protease is designated as Protease TCES.

An expression vector in which the entire Protease TCES gene is reconstituted by combining the two DNA fragments can be constructed. However, when using Escherichia coli as a host, a transformant into which the expression plasmid of interest had been introduced was not obtained, probably because the generation of the product expressed from the gene in cells may be harmful or lethal to Escherichia coli. In such a case, for example, it is possible to use Bacillus subtilis as a host for extracellular secretion of the protease and to determine the activity.

As a Bacillus subtilis strain, Bacillus subtilis DB104 can be used, which is a known strain as described in Gene, 83:215–233 (1989). As a cloning vector, the plasmid pUB18-P43 can be used, which is a generous gift from Dr. Sui-Lam Wong, University of Calgary. The plasmid contains a kanamycin-resistance gene as a selectable marker.

A recombinant plasmid in which the Protease TCES gene is inserted downstream the P43 promoter in the plasmid vector pUB18-P43 is designated as the plasmid pSTC3. Bacillus subtilis DB104 transformed with this plasmid is designated and indicated as Bacillus subtilis DB104/pSTC3, and was deposited on Dec. 1, 1995 (the date of the original deposit) under Budapest Treaty at the National Institute of Bioscience and Human-Technology, Agency of Industrial Science and Technology, Ministry of International Trade and Industry, 1–3, Higashi 1-chome, Tsukuba-shi, Ibaraki-ken, Japan under accession number FERM BP-5635.

The restriction enzyme map of the plasmid pSTC3 is shown in FIG. 1. In FIG. 1, the bold line indicates the DNA fragment inserted into the plasmid vector pUB18-P43.

A thermostable protease activity is found in either of the culture supernatant and the cell extract of the culture of Bacillus subtilis DB104/pSTC3.

Main properties of a crude enzyme preparation of the protease obtained from the culture of the transformant are as follows.

(1) Action:

Degrades casein and gelatin to generate short chain polypeptides.

Hydrolyzes succinyl-L-leucyl-L-leucyl-L-valyl-L-tyrosine-4-methylcoumarin-7-amide (Suc-Leu-Leu-Val-Tyr-MCA) SEQ ID NO:32 to generate a fluorescent substance (7-amino-4-methylcoumarin).

Hydrolyzes succinyl-L-alanyl-L-alanyl-L-prolyl-L-phenylalanine-p-nitroanilide (Suc-Ala-Ala-Pro-Phe-p-NA) SEQ ID NO:33 to generate a yellow substance (p-nitroaniline).

(2) Optimal temperature:

Exhibits an enzymatic activity at 37–95° C., with the optimal temperature being 70–80° C.

(3) Optimal pH:

Exhibits an enzymatic activity at pH 5.5–9, with the optimal pH being pH 7–8.

(4) Thermostability:

Retains 90% or more of its enzymatic activity after treatment at 80° C. for 3 hours.

When aligning the amino acid sequences of Protease PFUL, Protease TCES and a subtilisin (subtilisin BNP'; Nucl. Acids Res., 11:7911–7925 (1983)) such that homologous regions match each other as shown in FIGS. 2–5, it is found that, at the C-terminus and between the homologous regions of Protease PFUL, there are sequences which are not found in Protease TCES or the subtilisin. From these results, a protease having a molecular weight lower than that of Protease PFUL and similar to Protease TCES or subtilisins may exist in *Pyrococcus furiosus* in addition to Protease PFUL.

Thereupon, Southern hybridization against a chromosomal DNA prepared from *Pyrococcus furiosus* was carried out using a DNA probe from the homologous region, and a signal other than that for the Protease PFUL gene was observed, indicating the existence of another protease gene.

This novel protease gene can be isolated by the following procedure.

For example, a DNA fragment containing a gene encoding the novel protease is obtained by digesting a chromosomal DNA from *Pyrococcus furiosus* with an appropriate restriction enzyme and performing Southern hybridization against the digested DNA as described above. The base sequence of the DNA fragment is determined to confirm that the base sequence encodes an amino acid sequence homologous to the above-mentioned protease. If the DNA fragment does not contain the entire gene of interest, the remaining portion is further obtained by inverse PCR method or the like.

For example, when a chromosomal DNA from *Pyrococcus furiosus* is digested with restriction enzymes SacI and SpeI (Takara Shuzo) and is used for Southern hybridization, a signal of approximately 0.6 kb in size is observed. DNA fragments of this size are recovered, inserted between the SpeI-SacI sites in the plasmid vector pBluescript SK(–) (Stratagene), and *Escherichia coli* JM 109 is transformed with the resulting recombinant plasmids. A clone into which the fragment of interest is incorporated can be obtained from the transformants by colony hybridization using the same probe as that used for the Southern hybridization as described above. Whether or not the plasmid harbored by the obtained clone has the sequence that encodes the protease can be confirmed by determining the base sequence of the DNA fragment inserted into the plasmid. The presence of the protease gene in the plasmid was thus confirmed. This plasmid is designated as the plasmid pSS3.

It is found that the amino acid sequence deduced from the base sequence of the DNA fragment inserted into the plasmid pSS3 has homology with sequences of subtilisins, Protease PFUL, Protease TCES and the like. The product of the protease gene distinct from the Protease PFUL gene, a portion of which was newly obtained from *Pyrococcus furiosus* as described above, is designated as Protease PFUS. The regions which encode the N-terminal and C-terminal regions of the protease can be obtained by inverse PCR method.

Primers used for inverse PCR can be prepared based on the base sequence of the DNA fragment inserted into the plasmid pSS3. A chromosomal DNA from *Pyrococcus furiosus* is digested with an appropriate restriction enzyme, and the resulting DNA fragments are then subjected to an intramolecular ligation reaction. By performing PCR using the reaction mixture as a template and the above-mentioned primers, DNA fragments corresponding to the regions flanking the fragment for the protease gene contained in the plasmid pSS3 can be obtained. The amino acid sequence of the enzyme protein encoded by these regions can be deduced by analyzing the base sequences of the DNA fragments thus obtained. Furthermore, primers capable of amplifying the entire Protease PFUS gene using a chromosomal DNA from *Pyrococcus furiosus* as a template can be prepared. The primers NPF-4 and NPR-4 can be designed. The primer NPF-4 has the base sequence immediately upstream the initiation codon of the Protease PFUS gene and can introduce a BamHI site 5' to the sequence. The primer NPR-4 has a sequence complementary to the 3' portion of the Protease PFUS gene and can introduce a SphI site 5' to the sequence.

The base sequences of the primers NPF-4 and NPR-4 are shown in the SEQ ID NOS:13 and 14 of the Sequence Listing. These two primers can be used to amplify the entire Protease PFUS gene using a chromosomal DNA from *Pyrococcus furiosus* as a template.

Figure 6:
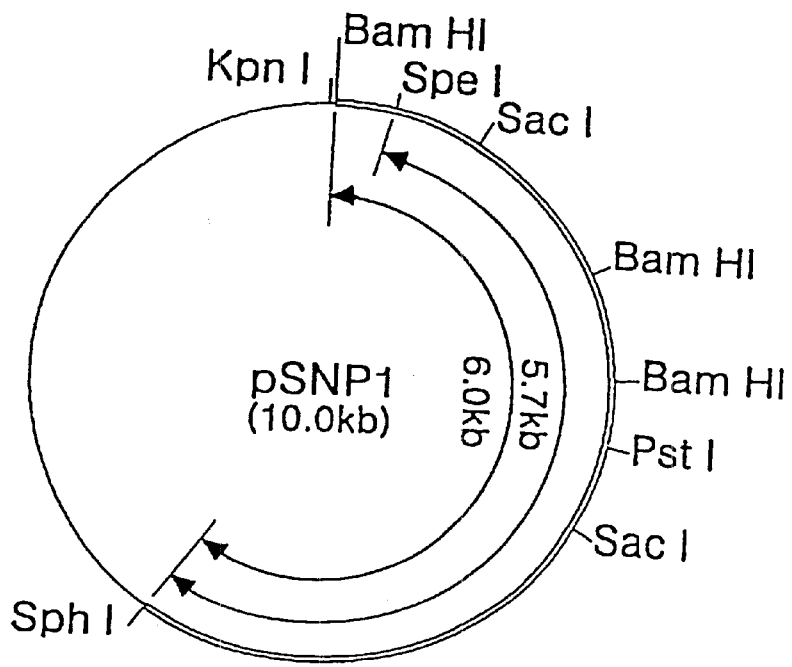
FIG. 6 is the restriction enzyme map of the plasmid pSNP1.

Like Protease TCES, Protease PFUS can be expressed in *Bacillus subtilis* as a host. A plasmid for expressing Protease PFUS can be constructed based on the expression plasmid for Protease TCES, pSTC3. Specifically, a plasmid for expressing Protease PFUS can be constructed by replacing the Protease TCES gene in the plasmid pSTC3 with the DNA fragment containing the entire Protease PFUS gene amplified by PCR with the primers as described above. The expression plasmid thus constructed is designated as the plasmid pSNP1. *Bacillus subtilis* DB104 transformed with this plasmid is designated and indicated as *Bacillus subtilis* DB104/pSNP1, and was deposited on Dec. 1, 1995 (the date of the original deposit) under Budapest Treaty at the National Institute of Bioscience and Human-Technology, Agency of Industrial Science and Technology, Ministry of International Trade and Industry, 1–3, Higashi 1-chome, Tsukuba-shi, Ibaraki-ken, Japan under accession number FERM BP-5634. The restriction enzyme map of the plasmid pSNP1 is shown in FIG. 6.

The base sequence corresponding to an open reading frame in the gene encoding Protease PFUS and the amino acid sequence of Protease PFUS deduced from the base sequence are shown in the SEQ ID NOS: 15 and 16 of the Sequence Listing, respectively.

A thermostable protease activity is found in either of the culture supernatant and the cell extract from the culture of *Bacillus subtilis* DB104/pSNP1. That is, a portion of the expressed Protease PFUS is secreted into the culture supernatant.

Main properties of the protease obtained from the culture of the transformant are as follows.

(1) Action:

Degrades casein and gelatin to generate short chain polypeptides.

Hydrolyzes succinyl-L-leucyl-L-leucyl-L-valyl-L-tyrosine-4-methylcoumarin-7-amide (Suc-Leu-Leu-Val-Tyr-MCA) SEQ ID NO:32 to generate a fluorescent substance (7-amino-4-methylcoumarin).

Hydrolyzes succinyl-L-alanyl-L-alanyl-L-prolyl-L-phenylalanine-p-nitroanilide (Suc-Ala-Ala-Pro-Phe-p-NA) SEQ ID NO:33 to generate a yellow substance (p-nitroaniline).

(2) Optimal Temperature:

Exhibits an enzymatic activity at 40–100° C., with the optimal temperature being 80–95° C.

(3) Optimal pH:

Exhibits an enzymatic activity at pH 5–10, with the optimal pH being pH 6–8.

(4) Thermostability:

Retains 90% or more of its enzymatic activity after treatment at 95° C. for 8 hours.

(5) pH Stability

Retains 95% or more of its activity after treatment at pH 5–11 at 95° C. for 60 minutes.

(6) Molecular Weight

Exhibits a molecular weight of approximately 45 kDa on SDS-PAGE.

Protease genes homologous to the Protease TCES gene and the Protease PFUS gene can be obtained from hyperthermophiles other than *Pyrococcus furiosus* and *Thermococcus celer* using a method similar to that used to obtain the Protease TCES gene and the Protease PFUS gene.

A DNA fragment of approximately 1 kb which encodes a sequence from the residue at position 323 to the residue at position 650 of the amino acid sequence of Protease PFUL as shown in the SEQ ID NO:6 of the Sequence Listing can be prepared and used as a probe for genomic Southern hybridization against chromosomal DNAs from *Staphylothermus marinus* DSM3639 and *Thermobacteroides proteoliticus* DSM 5265. As a result, signals are observed at the position of approximately 4.8 kb for the chromosomal DNA from *Staphylothermus marinus* digested with PstI (Takara Shuzo) and at the position of approximately 3.5 kb for the chromosomal DNA from *Thermobacteroides proteoliticus* digested with XbaI.

From these results, it proved that there are sequences homologous to those of the genes for Protease PFUL, Protease PFUS and Protease TCES and the like on the chromosomal DNAs from *Staphylothermus marinus* and *Thermobacteroides proteoliticus*. The genes encoding the hyperthermostable proteases in *Staphylothermus marinus* and *Thermobacteroides proteoliticus* can be isolated and identified from the DNA fragments thus detected by using a method similar to that used to isolate and identify the genes encoding Protease TCES and Protease PFUS.

In general, it is believed that use of a promoter that acts effectively in a host rather than a promoter that is inherently associated with the gene encoding the protein of interest would be advantageous in order to prepare a protein in a large quantity by genetic engineering technique. Although the P43 promoter used to construct the expression systems for Protease TCES and Protease PFUS is a promoter derived from *Bacillus subtilis*, it was not sufficiently effective to express the two proteases.

Thereupon, a gene that is expressed at high level in *Bacillus subtilis*, particularly a gene for a secreted protein, may be utilized in order to increase the expression level. Genes for α-amylase or various extracellular proteases can be used. For example, it is expected that use of a promoter and a signal peptide-encoding region of a subtilisin gene may increase the expression level of Protease PFUS.

Specifically, Protease PFUS can be expressed as a fused protein under control of the promoter of the subtilisin gene by placing the entire Protease PFUS gene downstream the region encoding the signal peptide of the subtilisin gene including the promoter region such that the translational frames of the two genes match each other.

For example, the gene encoding subtilisin E can be used as the subtilisin gene used in the present invention. The promoter and the signal peptide-encoding region of the subtilisin E gene inserted in the plasmid pKWZ as described in J. Bacteriol., 171:2657–2665 (1989) can be used. The base sequence of the 5' upstream region including the promoter sequence is described in the reference (supra) and the base sequence of the region encoding the subtilisin is described in J. Bacteriol., 158:411–418 (1984).

Based on these sequences, the primer SUB4 for introducing an EcoRI site upstream the promoter sequence of the gene and the primer BmR1 for introducing a BamHI site downstream the region encoding the signal peptide of subtilisin E are synthesized. The base sequences of the primers SUB4 and BmR1 are shown in the SEQ ID NOS:17 and 18 of the Sequence Listing, respectively. The primers SUB4 and BmR1 can be used to amplify a DNA fragment of approximately 0.3 kb containing the promoter and the signal peptide-encoding region of the subtilisin E gene by PCR using the plasmid pKWZ as a template.

The Protease PFUS gene to be placed downstream the DNA fragment can be obtained from a chromosomal DNA from *Pyrococcus furiosus* by PCR method. The primer NPF-4 can be used as a primer that hybridizes with the 5' region of the gene. The primer NPM-1, which is designed based on the base sequence downstream from the termination codon of the gene and has a SphI site, can be used as a primer which hybridizes with the 3' region of the gene. The sequence of the primer NPM-1 is shown in the SEQ ID NO:19 of the Sequence Listing.

One BamHI site present in the gene would become a problem for a procedure in which a BamHI site is utilized for joining the Protease PFUS gene to the 0.3 kb DNA fragment. The primers mutRR and mutFR for eliminating the BamHI site by PCR-mutagenesis method can be prepared based on the base sequence of the Protease PFUS gene as shown in the SEQ ID NO:15 of the Sequence Listing. The base sequences of the primers mutRR and mutFR are shown in the SEQ ID NOS:20 and 21 of the Sequence Listing, respectively. When these primers are used to eliminate the BamHI site, the amino acid residue encoded by this site, i.e., glycine at position 560 in the amino acid sequence of Protease PFUS as shown in the SEQ ID NO:16 of the Sequence Listing, is substituted by valine due to the base substitution introduced into the site.

The Protease PFUS gene to be joined to the promoter and the signal peptide-encoding region of the subtilisin E gene can be obtained by using these primers. Specifically, two PCRs are performed using a chromosomal DNA from *Pyrococcus furiosus* as a template and the pair of the primers mutRR and NPF-4 or the pair of the primers mutFR and NPM-1. In addition, a second round of PCR is performed using a heteroduplex formed by mixing the respective PCR-amplified DNA fragments as a template and the primers NPF-4 and NPM-1. Thus, the entire Protease PFUS gene of approximately 2.4 kb which does not contain an internal BamHI site can be amplified.

Figure 7:
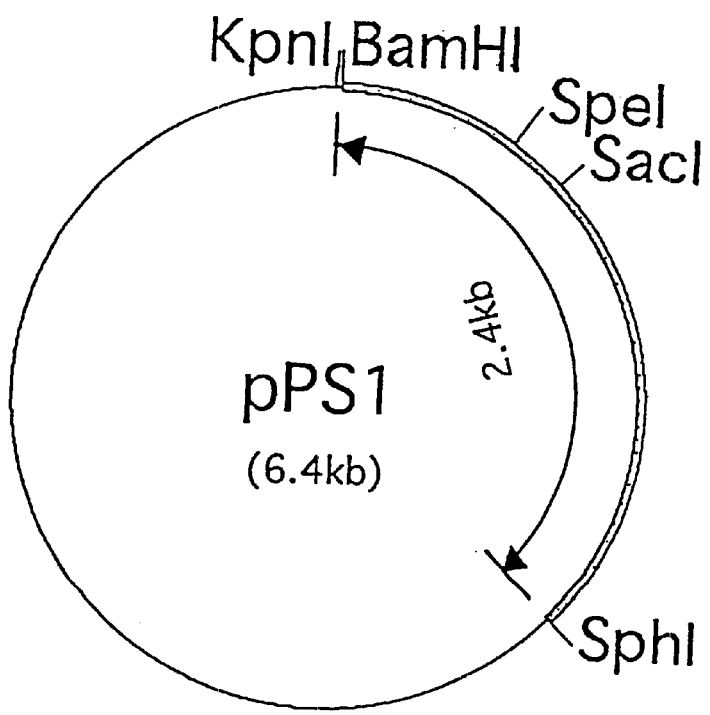
FIG. 7 is the restriction enzyme map of the plasmid pPS1.

A DNA fragment of approximately 2.4 kb obtained by digesting the PCR-amplified DNA fragment with BamHI and SphI is isolated and used to replace a BamHI-SphI fragment in the plasmid pSNP1 which contains the Protease PFUS gene. An expression vector thus constructed is designated as the plasmid pPS1. *Bacillus subtilis* DB104 transformed with this plasmid is designated as *Bacillus subtilis* DB104/pPS1. A similar protease activity is found in either of the culture supernatant and the cell extract of the culture of this transformant as observed for the transformant harboring the plasmid pSNP1, demonstrating that the amino acid substitution does not influence the enzymatic activity. The restriction enzyme map of the plasmid pPS1 is shown in FIG. 7.

Figure 8:
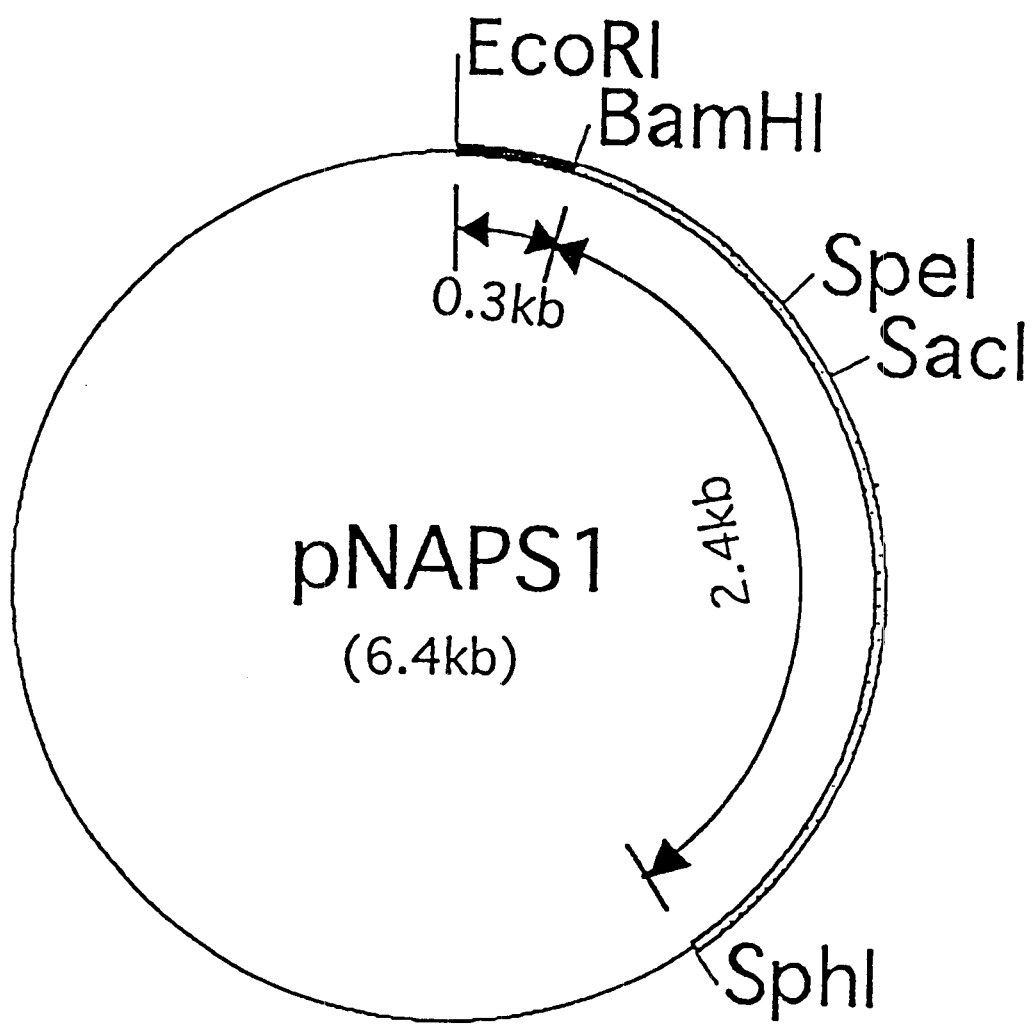
FIG. 8 is the restriction enzyme map of the plasmid pNAPS1.

The DNA fragment of approximately 0.3 kb containing the promoter and the signal peptide-encoding region of the subtilisin E gene is digested with EcoRI and BamHI and is used to replace the EcoRI-BamHI fragment containing the P43 promoter and a ribosome binding site in the plasmid pPS1. An expression plasmid thus constructed is designated as pNAPS1. *Bacillus subtilis* DB104 transformed with this plasmid is designated as *Bacillus subtilis* DB104/pNAPS1. A thermostable protease activity is found in either of the culture supernatant and the cell extract of the culture of the transformant, with the expression level being increased as compared with that of *Bacillus subtilis* DB104/pSNP1. The restriction enzyme map of the plasmid pNAPS1 is shown in FIG. 8.

The protease expressed from the transformant exhibits enzymological properties equivalent to those of the protease expressed by *Bacillus subtilis* DB104/pSNP1 as described above. The protease expressed by the transformant was purified. The analysis of the N-terminal amino acid sequence of the purified protease provided the amino acid sequence as shown in the SEQ ID NO:22 of the Sequence Listing. This sequence is identical with the sequence from position 133 to position 144 of the amino acid sequence of Protease PFUS as shown in the SEQ ID NO:16 of the Sequence Listing, indicating that the mature Protease PFUS is an enzyme consisting of a polypeptide starting from this portion. The amino acid sequence of the mature Protease PFUS assumed from these results is shown in the SEQ ID NO:4 of the Sequence Listing.

Although the amount of the protease produced by *Bacillus subtilis* DB104/pNAPS1 is increased as compared with the amount of the protease produced by *Bacillus subtilis* DB104/pSNP1 (FERM BP-5634), higher productivity is desired. It is expected that the expression level of the protease is increased by modifying the junction of the fused peptide encoded by pNAPS1 between the signal peptide of the subtilisin and Protease PFUS to make the removal of the signal peptide more efficient. In the plasmid pNAPS1, a peptide consisting of three amino acid residues Ala-Gly-Ser is inserted between the C-terminal amino acid residue of the signal peptide of subtilisin E as shown in the SEQ ID NO:3 of the Sequence Listing (Ala) and the N-terminal amino acid residue of Protease PFUS (Met). A transformant with increased expression level of the protease can be obtained by introducing a mutation into the DNA encoding this peptide in the plasmid pNAPS1 and examining the protease productivity of the transformant into which the mutant plasmid is introduced.

First, a mutant plasmid is prepared in which the portion encoding Ser in the three amino acid peptide in the gene encoding the fused protein, subtilisin E-Protease PFUS, in the plasmid pNAPS1 is modified such that the base sequence of the portion encodes random two amino acid residues. Such a mutant plasmid can be created by means of PCR. For example, the primers SPOF0 and SPOR0 having sequences in which the codon encoding Ser (TCC) is substituted by random six bases (the base sequences of the primers SPOF0 and SPOR0 are shown in the SEQ ID NOS:24 and 25 of the Sequence Listing, respectively) and the primers SUB3 and NPR-10 which are prepared based on the base sequence around this region (the base sequences of the primers SUB3 and NPR-10 are shown in the SEQ ID NOS:26 and 27 of the Sequence Listing, respectively) can be used to perform PCR to obtain a DNA fragment into which the intended mutation at the portion corresponding to the codon encoding Ser (TCC) is introduced. A mutant plasmid containing the protease gene with the introduced mutation can be obtained by replacing the resulting fragment for the corresponding region in the plasmid pNAPS1.

A transformant with increased expression level can be then obtained by introducing the mutant plasmids thus obtained into an appropriate host, for example, *Bacillus subtilis* DB104, and determining the level of the protease expressed by the transformants. The expression level of the protease can be confirmed by determining the activity in the independent culture of the isolated transformant. Alternatively, a transformant with increased expression level can be readily selected by using an agar plate containing a substrate.

Specifically, the transformants into which the mutant plasmids are introduced are grown on agar plates containing skim milk. Thereafter, the plates are incubated at temperature at which Protease PFUS exhibits its activity, for example, at 70° C. Skim milk around a colony of a transformant expressing a protease is degraded to become clear. The expression level of the protease can be estimated from the size of the clear zone.

One of the transformants thus obtained which express high level of protease activity as compared with *Bacillus subtilis* DB104/pNAPS1 is designated as *Bacillus subtilis* DB104/pSPO124. The plasmid contained in this transformant was prepared (this plasmid is designated as pSPO124). Analysis of the base sequence of the plasmid revealed that the portion encoding Ser was changed into a base sequence GGGAAT, that is, that a protein in which Ser was changed into Gly-Asn was encoded by the plasmid.

Thus, it proved that the expression level of the protein of interest can be increased in a bacterium of genus Bacillus as a host by placing a peptide consisting of four amino acid residues Ala-Gly-Gly-Asn (SEQ ID NO:30) downstream the signal peptide of a subtilisin, fusing it to the N-terminus of the protein of interest and expressing the fused protein. In addition to subtilisin E (from *Bacillus subtilis*) which is used in the present invention, subtilisin BPN' from *Bacillus amyloliquefaciens* (Nucl. Acids Res., 11:7911–7925 (1983)), subtilisin Carlsberg from *Bacillus licheniformis* (Nucl. Acids Res., 13:8913–8926 (1985)) and the like are known as subtilisins produced by bacteria of genus Bacillus. The signal peptides from them can be preferably used for the present invention although their amino acid sequences slightly vary each other. Various promoters which function in a bacterium of genus Bacillus can be used in place of the promoter from the subtilisin E gene which is used in the present invention for controlling expression.

There is no limitation regarding the protein to be expressed. It is possible to express a protein at high level by genetic engineering technique by applying the present invention as long as the gene for the protein is available. It is evident that the present invention can be utilized to express a protein derived from an organism other than the host from the fact that a protein derived from *Pyrococcus furiosus*, which is taxonomically different from bacteria of genus Bacillus, is expressed at high level. The present invention is preferably used to produce Protease PFUL, Protease TCES as well as proteases from *Staphylothermus marinus* and *Thermobacteroides proteoliticus* that are structurally similar to Protease PFUS by genetic engineering technique.

Based on the homology with subtilisins, it is considered that Protease PFUS is expressed as a precursor protein having a signal peptide and a propeptide and then subjected to processing to generate a mature enzyme. Furthermore, based on the results of the N-terminal amino acid sequence analysis of the mature Protease PFUS enzyme, it may be assumed that the mature enzyme is an enzyme consisting of the amino acid sequence as shown in the SEQ ID NO:4 of the Sequence Listing. However, the molecular weight of the purified mature Protease PFUS is approximately 45 kDa which is smaller than that calculated from the amino acid sequence, suggesting that Protease PFUS expressed as a precursor is converted to a mature protease after being subjected to processing of its C-terminal peptide as well.

If the C-terminal peptide removed by the processing is not essential to the enzymatic activity or the folding of the enzyme protein into proper structure, it is expected that the expression level of Protease PFUS can be also increased by deleting the region encoding this portion from the gene and expressing the protease.

The molecular weight of the mature Protease PFUS obtained from *Bacillus subtilis* DB104/pNAPS1 can be precisely measured, for example, by using a mass spectrometer. It is found from the measured molecular weight and the N-terminal amino acid sequence of the mature Protease PFUS determined as described above that the protease is a polypeptide corresponding to Ala at position 133 to Thr at position 552 of the amino acid sequence as shown in the SEQ ID NO:16 of the Sequence Listing. Furthermore, a plasmid which expresses Protease PFUS lacking a polypeptide nonessential for its enzymatic activity can be constructed by introducing a termination codon in the vicinity of the portion encoding Thr at position 552 in the Protease PFUS gene contained in the plasmid pNAPS1. Specifically, a DNA fragment having a base sequence into which the intended termination codon is introduced can be obtained by PCR using the primer NPR544 which can introduce a termination codon (TGA) on the C-terminal side of the 544th amino acid residue encoding codon from the initiation codon in the Protease PFUS gene in the plasmid pNAPS1 (Ser) (the base sequence of the primer NPR544 is shown in the SEQ ID NO:28 of the Sequence Listing) and the primer NPFE81 which has the base sequence of the region upstream from the NspV site in the gene (the base sequence of the primer NPFE81 is shown in the SEQ ID NO:29 of the Sequence Listing). A mutant plasmid containing the protease gene into which the mutation of interest is introduced can be then obtained by replacing the fragment for the corresponding region in the plasmid pNAPS1. This plasmid is designated as the plasmid PNAPSΔC. *Bacillus subtilis* DB104 transformed with this plasmid is designated as *Bacillus subtilis* DB104/pNAPSΔC.

This transformant expresses a protease activity having properties equivalent to those of Protease PFUS, with the expression level being higher than that of *Bacillus subtilis* DB104/pNAPS1.

Thus, it was found that the Protease PFUS gene contained in the plasmid pNAPSΔC has a sufficient region to express the activity of the enzyme. The base sequence of the region encoding Protease PFUS present in the plasmid is shown in the SEQ ID NO:2 of the Sequence Listing. The amino acid sequence encoded by the base sequence is shown in the SEQ ID NO:1 of the Sequence Listing.

Furthermore, Protease PFUS lacking its C-terminal peptide can be expressed by introducing a mutation similar to that in the plasmid pNAPSΔC into the Protease PFUS gene in the plasmid pSPO124.

Specifically, the plasmid of interest can be constructed by mixing and ligating a DNA fragment of approximately 13 kb obtained by digesting the plasmid pNAPSΔC with NspV and SphI with the plasmid pSPO124 that has been digested with NspV and SphI. This plasmid is designated as the plasmid pSO124ΔC. *Bacillus subtilis* DB104 transformed with this plasmid is designated and indicated as *Bacillus subtilis* DB104/pSO124ΔC, and deposited on May 16, 1997 (the date of the original deposit) under Budapest Treaty at the National Institute of Bioscience and Human-Technology, Agency of Industrial Science and Technology, Ministry of International Trade and Industry, 1–3, Higashi 1-chome, Tsukuba-shi, Ibaraki-ken, Japan under accession number FERM BP-6294. The expression level of protease of this transformant is increased as compared with that of *Bacillus subtilis* DB104/pNAPS1.

The enzymological properties as well as the physical and chemical properties of the proteases produced by the transformants, *Bacillus subtilis* DB104/pNAPSΔC and *Bacillus subtilis* DB104/pSPO124ΔC appear to be identical with those of the protease produced by *Bacillus subtilis* DB104/pSNP1. The main properties of the proteases obtained from the cultures of the two transformants are as follows:

(1) Action:

Degrades casein and gelatin to generate short chain polypeptides.

Hydrolyzes succinyl-L-leucyl-L-leucyl-L-valyl-L-tyrosine-4-methylcoumarin-7-amide (Suc-Leu-Leu-Val-Tyr-MCA) SEQ ID NO:32 to generate a fluorescent substance (7-amino-4-methylcoumarin).

Hydrolyzes succinyl-L-alanyl-L-alanyl-L-prolyl-L-phenylalanine-p-nitroanilide (Suc-Ala-Ala-Pro-Phe-p-NA) SEQ ID NO:33 to generate a yellow substance (p-nitroaniline).

(2) Optimal Temperature:

Exhibits an enzymatic activity at 40–110° C., with the optimal temperature being 80–95° C.

(3) Optimal pH:

Exhibits an enzymatic activity at pH 5–10, with the optimal pH being pH 6–8.

(4) Thermostability:

Retains 90% or more of its enzymatic activity after treatment at 95° C. for 8 hours.

(5) pH Stability

Retains 95% or more of its activity after treatment at pH 5–11 at 95° C. for 60 minutes.

(6) Molecular Weight

Exhibits a molecular weight of approximately 45 kDa on SDS-PAGE.

Thus, proteases having high thermostability and genes therefor are provided. Also, a novel system for expressing a protein, which enables the expression of the protease in large quantity is disclosed by the present invention. The expression system is useful in production of the protease of the present invention as well as various proteins by genetic engineering technique.

The following Examples illustrate the present invention in more detail, but are not to be construed to limit the scope thereof.

EXAMPLE 1

(1) Preparation of a Chromosomal DNA from *Pyrococcus furiosus*

*Pyrococcus furiosus* DSM3638 was cultured as follows.

A medium containing 1% Tryptone, 0.5% yeast extract, 1% soluble starch, 3.5% Jamarine S Solid (Jamarine Laboratory), 0.5% Jamarine S Liquid (Jamarine Laboratory), 0.003% $MgSO_4$, 0.001% NaCl, 0.0001% $FeSO_4 \cdot 7H_2O$, 0.0001% $CoSO_4$, 0.0001% $CaCl_2 \cdot 7H_2O$, 0.0001% ZnSO$_4$, 0.1 ppm CuSO$_4$·5H$_2$O, 0.1 ppm H$_3$BO'3, 0.1 ppm KAl(SO$_4$)$_2$, 0.1 ppm Na$_2$MoO$_4$·2H$_2$O, 0.25 ppm NiCl$_2$·H$_2$O was placed in a 2 L medium bottle, sterilized at 120° C. for 20 minutes, bubbled with nitrogen gas to remove dissolved oxygen, then the strain was inoculated into the medium and cultured at 95° C. for 16 hours without shaking. After cultivation, cells were collected by centrifugation.

The resulting cells were then suspended in 4 mL of 50 mM Tris-HCl (pH 8.0) containing 25% sucrose. 2 mL of 0.2 M EDTA and 0.8 mL of lysozyme (5 mg/mL) were added to the suspension. The mixture was incubated at 20° C. for 1 hour. 24 mL of SET solution (150 mM NaCl, 1 mM EDTA, 20 mM Tris-HCl, pH 8.0), 4 mL of 5% SDS and 400 µL of proteinase K (10 mg/mL) were then added to the mixture. Incubation was further carried out at 37° C. for 1 hour. The reaction was terminated by extracting the mixture with phenol-chloroform. Then, ethanol precipitation was carried out to obtain approximately 3.2 mg of chromosomal DNA.

EXAMPLE 2

(1) Synthesis of Primers for Constructing the Plasmid pNSP1

In order to synthesize primers used to amplify the entire Protease PFUS gene, the plasmid pSNP1 that contains the entire gene was isolated from *Bacillus subtilis* DB104/pSNP1 (FERM BP-5634) and the base sequence of the required region was determined. Based on the base sequence, the primer NPF-4 for introducing a BamHI site immediately upstream the initiation codon of the Protease PFUS gene and the primer NPM-1 which hybridizes with the 3' region of the gene and contains a recognition site for SphI were synthesized. The base sequences of the primers NPF-4 and NPM-1 are shown in the SEQ ID NOS:13 and 19 of the Sequence Listing, respectively.

The primers mutRR and mutFR for removing the BamHI site present approximately 1.7 kb downstream from the initiation codon in the Protease PFUS gene were also synthesized. The base sequences of the primers mutRR and mutFR are shown in the SEQ ID NOS:20 and 21 of the Sequence Listing, respectively.

(2) Preparation of the Plasmid pPS1

Two sets of LA-PCR reaction mixtures each of which containing a chromosomal DNA from *Pyrococcus furiosus* as a template and a combination of the primers NPF-4 and mutRR or a combination of the primers mutFR and NPM-1 were prepared and subjected to 30 cycles of reactions of 94° C. for 30 seconds—55° C. for 1 minute—68° C. for 3 minutes. LA PCR Kit Ver. 2 (Takara Shuzo) was used to prepare the LA-PCR reaction mixtures. Aliquots of the reaction mixtures were subjected to agarose gel electrophoresis, and amplification of a DNA fragment of approximately 1.8 kb with the primers NPF-4 and mutRR and a DNA fragment of approximately 0.6 kb with the primers mutFR and NPM-1 were observed, respectively.

The primers were removed from the two PCR reaction mixtures using SUPREC-02 (Takara Shuzo) to prepare amplified DNA fragments. An LA-PCR reaction mixture which contained these two amplified DNA fragments and did not contain the primers or LA Taq was prepared, heat-denatured at 94° C. for 10 minutes, cooled to 30° C. within 30 minutes, then incubated at 30° C. for 15 minutes to form a heteroduplex. Subsequently, LA Taq (Takara Shuzo) was added to the reaction mixture to react at 72° C. for 30 minutes. The primers NPF-4 and NPM-1 were then added to the reaction mixture, which was then subjected to 25 cycles of reactions of 94° C. for 30 seconds—55° C. for 1 minute—68° C. for 3 minutes. Amplification of a DNA fragment of approximately 2.4 kb was observed in the reaction mixture.

The DNA fragment of approximately 2.4 kb was digested with BamHI and SphI (both from Takara Shuzo). The fragment was mixed and ligated with the plasmid pSNP1 which had been digested with BamHI and SphI to remove the entire Protease PFUS gene, then introduced into *Bacillus subtilis* DB104. Plasmids were prepared from resulting kanamycin-resistant transformants, and a plasmid into which only one molecule of the fragment of approximately 2.4 kb was inserted was selected and designated as the plasmid pPS1. *Bacillus subtilis* DB104 transformed with this plasmid pPS1 was designated as *Bacillus subtilis* DB104/pPS1.

The restriction enzyme map of the plasmid pPS1 is shown in FIG. 7.

(3) Amplification of a DNA Fragment for the Promoter-signal Peptide-encoding Region of the Subtilisin E Gene Primers for obtaining the promoter-signal peptide-encoding region of the subtilisin E gene were synthesized. First, the primer SUB4 was synthesized based on the base sequence of the promoter region of the subtilisin E gene as described in J. Bacteriol., 171:2657–2665 (1989), which hybridizes with the sequence upstream this region and contains an EcoRI site (the base sequence of the primer SUB4 is shown in the SEQ ID NO:17 of the Sequence Listing). The primer BmR1 which is capable of introducing a BamHI site immediately downstream the signal peptide-encoding region was synthesized based on the base sequence of the subtilisin E gene as described in J. Bacteriol., 158:411–418 (1984) (the base sequence of the primer BmR1 is shown in the SEQ ID NO:18 of the Sequence Listing).

A PCR reaction mixture containing the plasmid pKWZ, which contains the subtilisin E gene as described in J. Bacteriol., 171:2657–2665, as a template and the primers SUB4 and BmR1 was prepared and subjected to 30 cycles of reactions of 94° C. for 30 seconds—55° C. for 1 munute—68° C. for 2 minutes. An aliquot of the reaction mixture was subjected to agarose gel electrophoresis, and amplification of a DNA fragment of approximately 0.3 kb was observed.

(4) Construction of the Protease Expression Plasmid pNAPS1

The DNA fragment of approximately 0.3 kb as described above was digested with EcoRI (Takara Shuzo) and BamHI, mixed and ligeted with the plasmid pPS1 described in Example 3 which had been digested with EcoRI and BamHI, then introduced into *Bacillus subtilis* DB104. Plasmids were prepared from resulting kanamycin-resistant transformants, and a plasmid into which only one molecule of the fragment of approximately 0.3 kb was inserted was selected and designated as the plasmid pNAPS1. *Bacillus subtilis* DB104 transformed with the plasmid pNAPS1 was designated as *Bacillus subtilis* DB104/pNAPS1.

The restriction enzyme map of the plasmid pNAPS1 is shown in FIG. 8.

(5) Construction of the Plasmid pSNP2

The primer SUB17R for introducing a BamHI site upstream the signal peptide-encoding region of the subtilisin E gene in the above-mentioned plasmid pNAPS1 was synthesized (the base sequence of the primer SUB17R is shown in the SEQ ID NO:23 of the Sequence Listing). A PCR reaction mixture containing the plasmid pNAPS1 as a template and the primers SUB17R and SUB4 was prepared and subjected to 25 cycles of reactions of 94° C. for 30 seconds—55° C. for 1 munute—72° C. for 1 minute. The amplified DNA fragment of approximately 0.21 kb was digested with EcoRI and BamHI to obtain a DNA fragment of approximately 0.2 kb that contains the promoter and the SD sequence of the subtilisin E gene. This fragment was mixed and ligated with the plasmid pNAPS1 that had been digested with EcoRI and BamHI. The reaction mixture was used to transform *Bacillus subtilis* DB104. Plasmids were prepared from resulting kanamycin-resistant transformants, and a plasmid into which the DNA fragment of approximately 0.2 kb was inserted was selected and designated as the plasmid pSNP2.

(6) Generation of a Mutant Plasmid which Expresses a Protease at High Level

The primers SPOF0 and SPOR0 for substituting the sequence encoding the amino acid residue Ser (base sequence: TCC) at the junction between the signal peptide-encoding region of the subtilisin E gene in the plasmid pNAPS1 and the initiation codon of the Protease PFUS gene with a sequence for two random amino acid residues were synthesized (the base sequences of the primers SPOF0 and SPOR0 are shown in the SEQ ID NOS:24 and 25 of the Sequence Listing, respectively). The primer SUB3 for introducing a BamHI site immediately upstream the signal peptide-encoding region in the subtilisin E gene in the plasmid pNAPS1 and the primer NPR-10 which contains a SpeI site within the Protease PFUS encoding region were synthesized (the base sequences of the primers SUB3 and NPR-10 are shown in the SEQ ID NOS:26 and 27 of the Sequence Listing, respectively).

PCR reaction mixtures each of which containing the plasmid pNAPS1 as a template and a combination of the primers SPOF0 and NPR-10 or a combination of the primers SUB3 and SPOR0 were prepared and subjected to 20 cycles of reactions of 94° C. for 30 seconds—50° C. for 1 munute—72° C. for 1 minute. DNA fragments of approximately 0.13 kb and approximately 0.35 kb amplified in the two reaction mixtures were mixed together, denatured at 94° C. for 10 minutes, cooled gradually to 37° C. to form a heteroduplex. A double-stranded DNA was then generated from the heteroduplex by means of Taq polymerase (Takara Shuzo). A PCR reaction mixture containing the double-stranded DNA thus obtained as a template and the primers SUB3 and NPR-10 was prepared and subjected to 25 cycles of reactions of 94° C. for 30 seconds—50° C. for 1 minute—72° C. for 1 minute. A DNA fragment obtained by digesting the amplified DNA fragment of approximately 0.43 kb with BamHI and SpeI (Takara Shuzo) was mixed and ligated with the plasmid pSNP2 that had been digested with BamHI and SpeI. The reaction mixture was used to transform *Bacillus subtilis* DB104.

Resulting kanamycin-resistant transformants were inoculated on skim milk plates (LB-agar medium for high temperature cultivation containing 10 μg/mL of kanamycin and 1% skim milk) to form colonies. Subsequently, the plates were incubated at 70° C. and the protease activities expressed by the respective transformants were examined based on the degree of degradation of the skim milk around the colonies. As a result, one clone that exhibited a particularly high activity was isolated and a plasmid, which was designated as the plasmid pSPO124, was prepared from the clone. *Bacillus subtilis* DB104 transformed with this plasmid was designated as *Bacillus subtilis* DB104/pSPO124. The base sequence of the plasmid pSPO124 was analyzed, and it was found that the base sequence which encodes Ser in the plasmid pNAPS1 was substituted by a base sequence GGGAAT, that is, that a protein in which Ser was changed to two amino acid residues Gly-Asn was encoded. Additionally, it proved that the 25th codon from the initiation codon corresponding to Pro (CCA) of the Protease PFUS gene was changed to a codon encoding Leu (CTA) simultaneously with the mutation as described above.

(7) Construction of the Protease Expression Plasmid pNAPSΔC

A termination codon was introduced on the C-terminal side of the 544th amino acid residue from the initiation codon of the Protease PFUS gene in the plasmid pNAPS1 to construct a plasmid which expresses a protease lacking downstream from this site. The primer NPR544 which introduces a termination codon (base sequence: TGA) on the C-terminal side of the codon encoding the 544th amino acid residue in the gene and has an SphI site was synthesized (the base sequence of the primer NPR544 is shown in the SEQ ID NO:28 of the Sequence Listing). In addition, the primer NPFE81 was synthesized based on the base sequence of the portion upstream from the NspV site in the gene (the base sequence of the primer NPFE81 is shown in the SEQ ID NO:29 of the Sequence Listing).

A PCR reaction mixture containing the plasmid pNAPS1 as a template and the primers NPFE81 and NPR544 was prepared and subjected to 20 cycles of reactions of 94° C. for 30 seconds—50° C. for 1 minute—72° C. for 1 minute. The amplified DNA fragment of approximately 0.61 kb was digested with NspV (Takara Shuzo) and SpeI to obtain a DNA fragment of approximately 0.13 kb containing the termination codon. This DNA fragment was mixed and ligated with the plasmid pNAPS1 that had been digested with restriction enzymes NspV and SphI. The reaction mixture was used to transform *Bacillus subtilis* DB104. Plasmids were prepared from the resulting kanamycin-resistant transformants, a plasmid into which the DNA fragment of approximately 0.13 kb was inserted was selected and designated as the plasmid pNAPSΔC. *Bacillus subtilis* DB104 transformed with the plasmid pNAPSΔC was designated as *Bacillus subtilis* DB104/pNAPSΔC.

(8) Construction of the Protease Expression Plasmid pSPO124ΔC

A DNA fragment of approximately 1.3 kb obtained by digesting the plasmid pNAPSΔC with NspV and SphI was isolated, then mixed and ligated with the plasmid pSPO124 that had been digested with NspV and SphI. The reaction mixture was used to transform *Bacillus subtilis* DB104. Plasmids were prepared from the resulting kanamycin-resistant transformants, a plasmid into which the DNA fragment of approximately 1.3 kb was inserted was selected and designated as the plasmid pSPO124ΔC. *Bacillus subtilis* DB104 transformed with the plasmid pSPO124ΔC was designated as *Bacillus subtilis* DB104/pSPO124ΔC.

EXAMPLE 3

(1) Cultivation of *Bacillus subtilis* Transformed with a Plasmid Containing the Protease PFUS Gene and Preparation of a Crude Enzyme Solution

*Bacillus subtilis* DB104/pNAPS1, which is *Bacillus subtilis* DB104 into which the plasmid pNAPS1 containing the Protease PFUS gene was introduced as described in Example 2, was cultured in 2 mL of LB medium (Tryptone 10 g/L, yeast extract 5g/L, NaCl 5g/L, pH 7.2) containing 10 µg/mL of kanamycin at 37° C. for 24 hours. The culture was centrifuged to obtain a culture supernatant (the preparation 1-S) and cells.

The cells were suspended in 100 µL of 50 mM Tris-HCl, pH 7.5 and digested at 37° C. for 45 minutes after an addition of 2 mg of lysozyme (Sigma). The digested sample was heat-treated at 95° C. for 10 minutes, and then a supernatant was collected by centrifugation to obtain a cell-free extract (the preparation 1-L).

Similarly, culture supernatants and cell-free extracts were obtained from *Bacillus subtilis* DB104/pSPO124 containing the plasmid pSPO124, *Bacillus subtilis* DB104/pNAPSΔC containing the plasmid pNAPSΔC or *Bacillus subtilis* DB104/pSPO124ΔC containing the plasmid pSPO124ΔC. The culture supernatant and the cell-free extract from *Bacillus subtilis* DB104/pSPO124 were designated as 124-S and 124-L, respectively. The culture supernatant and the cell-free extract from *Bacillus subtilis* DB104/pNAPSΔC were designated as ΔC-S and ΔC-L, respectively. The culture supernatant and the cell-free extract from *Bacillus subtilis* DB104/pSPO124ΔC were designated as 124ΔC-S and 124ΔC-L, respectively. Protease activities were determined with these preparations and the concentration of the protease contained in each preparation was determined.

(2) Comparison of Protease Productivities

The activity of Protease PFUS was determined by spectroscopically measuring the amount of p-nitroaniline generated in an enzymatic hydrolysis reaction using Suc-Ala-Ala-Pro-Phe-p-NA (Sigma) (SEQ ID NO:33) as a substrate. Briefly, an enzyme preparation to be measured for its enzymatic activity was appropriately diluted. 50 µL of 1 mM Suc-Ala-Ala-Pro-Phe-p-NA (SEQ ID NO:33) solution in 100 mM phosphate buffer, pH 7.0 was added to 50 µL of the diluted sample solution. Then, the reaction was allowed to proceed at 95° C. for 30 minutes. After terminating the reaction by cooling on ice, absorbance at 405 nm was measured to calculate the amount of p-nitroaniline generated. One unit of the enzyme was defined as the amount of the enzyme which generated 1 lmole of p-nitroaniline per 1 minute at 95° C. The amount of enzyme protein expressed in the culture supernatant or the cells was calculated based on the measured enzymatic activity assuming the specific activity as 9.5 unit/mg protein of Protease PFUS.

The protease activity of each enzyme preparation prepared in Example 3-(1) was measured. The productivity of Protease PFUS per 1 L of culture of each transformant calculated from the measurement is shown in Table 1.

In *Bacillus subtilis* DB104/pSPO124, the productivity of Protease PFUS in the cells increased by 3.6 fold as compared with that of *Bacillus subtilis* DB104/pNAPS1. In *Bacillus subtilis* DB104/pNAPSΔC, the productivity of Protease PFUS increased in the culture supernatant by 2.4 fold and in the cells by 2.2 fold, respectively. Also, in *Bacillus subtilis* DB104/pSPO124ΔC, the productivity of Protease PFUS increased in the culture supernatant by 2 fold and in the cells by 2.4 fold, respectively. The productivity per cells also increased.

The total amount of Protease PFUS produced in the culture supernatant and the cells increased by 2.1 fold for *Bacillus subtilis* DB104/pSPO124, by 2.1 fold for *Bacillus subtilis* DB104/pNAPSΔC and by 2.2 fold for *Bacillus subtilis* DB104/pSPO124ΔC, respectively, as compared with that of *Bacillus subtilis* DB104/pNAPS1.

TABLE 1

The productivity of Protease PFUS (mg/L of culture)

| Transformant (Plasmid) | Culture Supernatant | Cells | Culture Supernatant + Cells |
|---|---|---|---|
| pNAPS1 | 15.1 | 12.5 | 27.6 |
| pSPO124 | 13.1 | 45.4 | 58.5 |
| pNAPSΔC | 35.5 | 28.1 | 63.6 |
| pSPO124ΔC | 30.5 | 30.1 | 60.6 |

EXAMPLE 4

(1) Preparation of Purified Enzyme Preparation of the Mature Protease PFUS

*Bacillus subtilis* DB104/pNAPS1 and *Bacillus subtilis* DB104/pSPO124ΔC, both of which are *Bacillus subtilis* DB104 into which the gene for the hyperthermostable protease of the present invention was introduced as described in Example 2, were separately inoculated into 5 mL of LB medium containing 10 µg/mL kanamycin and cultured with shaking at 37° C. for 7 hours. The cultures of 5 mL were inoculated into 500 mL of TM medium (soybean powder 5 g/L, Polypeptone 10 g/L, meat extract 5 g/L, yeast extract 2 g/L, glucose 10 g/L, FeSO$_4$·7H$_2$O 10 mg/L, MnSO$_4$·4H$_2$O 10 mg/L, ZnSO$_4$·7H$_2$O 1 mg/L, pH 7.0) containing 10 µg/mL of kanamycin in 5 L Erlenmeyer flasks and cultured with shaking at 30° C. for 3 days. The resulting cultures were sonicated, heat-treated at 95° C. for 30 minutes, then centrifuged to collect supernatants. Ammonium sulfate was added to the supernatants to 25% saturation, then the supernatants obtained by subsequent centrifugation were applied to Micro-Prep Methyl HIC columns (Bio-Rad) equilibrated with 25 mM Tris-HCl buffer (pH 7.6) containing 25% saturated ammonium sulfate. After washing the gel with the same buffer, Protease PFUS adsorbed to the columns was eluted by stepwise elution using 25 mM Tris-HCl buffer (pH 7.6) containing 40% ethanol. The fractions containing Protease PFUS thus obtained were subjected to gel filtration using NAP-25 columns (Pharmacia) equilibrated with 0.05% trifluoroacetic acid containing 20% acetonitrile, desalted while denaturing Protease PFUS, then purified preparations of Protease PFUS were obtained. The preparations obtained from *Bacillus subtilis* DB104/pNAPS1 and *Bacillus subtilis* DB104/pSPO124ΔC were designated as NAPS-1 and SPO-124ΔC, respectively.

Electrophoresis of both of the purified enzyme preparations on 0.1% SDS-10% polyacrylamide gel followed by staining with Coomassie Brilliant Blue R-250 revealed single bands for both of the purified enzyme preparations NAPS-1 and SPO-124ΔC with an estimated molecular weight of approximately 45 kDa.

(2) Analysis of the N-terminal Amino Acid Sequence of the Mature Protease PFUS

N-terminal amino acid sequences of the purified enzyme preparations NAPS-1 and SPO-124ΔC were analyzed by automated Edman method using G1000A protein sequencer (Hewlett-Packard). Both of the N-terminal amino acid sequences of the two purified enzyme preparations were as shown in the SEQ ID NO:22 of the Sequence Listing. This sequence coincides with the sequence from position 133 to position 144 of the amino acid sequence of Protease PFUS as shown in the SEQ ID NO:16 of the Sequence Listing, indicating that both of NAPS-1 and SPO-124ΔC are enzymes consisting of a polypeptide starting from this portion.

(3) Mass Spectrometric Analysis of the Mature Protease PFUS

Mass spectrometric analysis on the purified enzyme preparations NAPS-1 and SPO-124ΔC was carried out using API300 quadrupole triple mass spectrometer (Perkin-Elmer Sciex). Based on the estimated molecular weight of NAPS-1, 43,744 Da, it was demonstrated that the mature Protease PFUS produced by *Bacillus subtilis* DB104/pNAPS1 is an enzyme consisting of a polypeptide from Ala at position 133 to Thr at position 552 of the amino acid sequence of Protease PFUS as shown in the SEQ ID NO:16 of the Sequence Listing. Furthermore, based on the estimated molecular weight of SPO-124ΔC, 42,906 Da, it was demonstrated that the mature Protease PFUS produced by *Bacillus subtilis* DB104/pSPO124ΔC is an enzyme consisting of a polypeptide from Ala at position 133 to Ser at position 544 of the amino acid sequence of Protease PFUS as shown in the SEQ ID NO:16 of the Sequence Listing, i.e., the amino acid sequence as shown in the SEQ ID NO:1 of the Sequence Listing.

What is claimed is:

1. An isolated protease consisting of an amino acid sequence in which one or more amino acid residues are deleted from the C-terminus of the amino acid sequence represented by SEQ ID NO:4 and having a thermostable protease activity, wherein said protease comprises the amino acid sequence represented by SEQ ID NO:1.

2. The protease according to claim 1, which consists of the amino acid sequence represented by SEQ ID NO:1.

* * * * *

```
                      SEQUENCE LISTING

<160> NUMBER OF SEQ ID NOS: 33

<210> SEQ ID NO 1
<211> LENGTH: 412
<212> TYPE: PRT
<213> ORGANISM: Pyrococcus furiosus

<400> SEQUENCE: 1

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
                20                  25                  30

Ile Asp Thr Gly Ile Asp Ala Ser His Pro Asp Leu Gln Gly Lys Val
            35                  40                  45

Ile Gly Trp Val Asp Phe Val Asn Gly Arg Ser Tyr Pro Tyr Asp Asp
        50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
```

```
                    260                 265                 270
     Thr Ala Leu Ile Glu Thr Ala Asp Ile Val Lys Pro Asp Glu Ile Ala
                 275                 280                 285

Asp Ile Ala Tyr Gly Ala Gly Arg Val Asn Ala Tyr Lys Ala Ile Asn
                 290                 295                 300

Tyr Asp Asn Tyr Ala Lys Leu Val Phe Thr Gly Tyr Val Ala Asn Lys
     305                 310                 315                 320

Gly Ser Gln Thr His Gln Phe Val Ile Ser Gly Ala Ser Phe Val Thr
                     325                 330                 335

Ala Thr Leu Tyr Trp Asp Asn Ala Asn Ser Asp Leu Asp Leu Tyr Leu
                 340                 345                 350

Tyr Asp Pro Asn Gly Asn Gln Val Asp Tyr Ser Tyr Thr Ala Tyr Tyr
                 355                 360                 365

Gly Phe Glu Lys Val Gly Tyr Tyr Asn Pro Thr Asp Gly Thr Trp Thr
                 370                 375                 380

Ile Lys Val Val Ser Tyr Ser Gly Ser Ala Asn Tyr Gln Val Asp Val
     385                 390                 395                 400

Val Ser Asp Gly Ser Leu Ser Gln Pro Gly Ser Ser
                     405                 410
```

<210> SEQ ID NO 2
<211> LENGTH: 1236
<212> TYPE: DNA
<213> ORGANISM: Artificial Sequence
<220> FEATURE:
<223> OTHER INFORMATION: Synthetic

<400> SEQUENCE: 2

```
gcagaattag aaggactgga tgagtctgca gctcaagtta tggcaactta cgtttggaac      60
ttgggatatg atggttctgg aatcacaata ggaataattg acactggaat tgacgcttct    120
catccagatc tccaaggaaa agtaattggg tgggtagatt ttgtcaatgg taggagttat    180
ccatacgatg accatggaca tggaactcat gtagcttcaa tagcagctgg tactggagca    240
gcaagtaatg gcaagtacaa gggaatggct ccaggagcta agctggcggg aattaaggtt    300
ctaggtgccg atggttctgg aagcatatct actataatta agggagttga gtgggccgtt    360
gataacaaag ataagtacgg aattaaggtc attaatcttt ctcttggttc aagccagagc    420
tcagatggta ctgacgctct aagtcaggct gttaatgcag cgtgggatgc tggattagtt    480
gttgtggttg ccgctggaaa cagtggacct aacaagtata caatcggttc tccagcagct    540
gcaagcaaag ttattacagt tggagccgtt gacaagtatg atgttataac aagcttctca    600
agcagagggc caactgcaga cggcaggctt aagcctgagg ttgttgctcc aggaaactgg    660
ataattgctg ccagagcaag tggaactagc atgggtcaac caattaatga ctattacaca    720
gcagctcctg ggacatcaat ggcaactcct cacgtagctg gtattgcagc cctcttgctc    780
caagcacacc cgagctggac tccagacaaa gtaaaaacag ccctcataga aactgctgat    840
atcgtaaagc cagatgaaat agccgatata gcctacggtg caggtagggt taatgcatac    900
aaggctataa actacgataa ctatgcaaag ctagtgttca ctggatatgt tgccaacaaa    960
ggcagccaaa ctcaccagtt cgttattagc ggagcttcgt tcgtaactgc cacattatac   1020
tgggacaatg ccaatagcga ccttgatctt tacctctacg atcccaatgg aaaccaggtt   1080
gactactctt acaccgccta ctatggattc gaaaaggttg gttattacaa cccaactgat   1140
ggaacatgga caattaaggt tgtaagctac agcggaagtg caaactatca agtagatgtg   1200
```
gtaagtgatg gttcccttc acagcctgga agttca    1236

<210> SEQ ID NO 3
<211> LENGTH: 29
<212> TYPE: PRT
<213> ORGANISM: Bacillus subtilis

<400> SEQUENCE: 3

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala
            20                  25

<210> SEQ ID NO 4
<211> LENGTH: 522
<212> TYPE: PRT
<213> ORGANISM: Pyrococcus furiosus
<220> FEATURE:
<221> NAME/KEY: misc_feature
<222> LOCATION: (428)..(428)
<223> OTHER INFORMATION: Xaa at position 428 is Gly or Val.

<400> SEQUENCE: 4

Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
        115                 120                 125

Lys Val Ile Asn Leu Ser Leu Gly Ser Ser Gln Ser Ser Asp Gly Thr
    130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175

Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
        195                 200                 205

Arg Leu Lys Pro Glu Val Val Ala Pro Gly Asn Trp Ile Ile Ala Ala
    210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

-continued

```
Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
    290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Gly Phe Glu Lys Val Gly Tyr Tyr Asn Pro Thr Asp Gly Thr Trp Thr
    370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser Pro Ser Pro Gln
                405                 410                 415

Pro Glu Pro Thr Val Asp Ala Lys Thr Phe Gln Xaa Ser Asp His Tyr
            420                 425                 430

Tyr Tyr Asp Arg Ser Asp Thr Phe Thr Met Thr Val Asn Ser Gly Ala
        435                 440                 445

Thr Lys Ile Thr Gly Asp Leu Val Phe Asp Thr Ser Tyr His Asp Leu
    450                 455                 460

Asp Leu Tyr Leu Tyr Asp Pro Asn Gln Lys Leu Val Asp Arg Ser Glu
465                 470                 475                 480

Ser Pro Asn Ser Tyr Glu His Val Glu Tyr Leu Thr Pro Ala Pro Gly
                485                 490                 495

Thr Trp Tyr Phe Leu Val Tyr Ala Tyr Tyr Thr Tyr Gly Trp Ala Tyr
            500                 505                 510

Tyr Glu Leu Thr Ala Lys Val Tyr Tyr Gly
        515                 520

<210> SEQ ID NO 5
<211> LENGTH: 4765
<212> TYPE: DNA
<213> ORGANISM: Artificial Sequence
<220> FEATURE:
<223> OTHER INFORMATION: Synthetic

<400> SEQUENCE: 5
tttaaattat aagatataat cactccgagt gatgagtaag atacatcatt acagtcccaa      60
aatgtttata attggaacgc agtgaatata caaaatgaat ataacctcgg aggtgactgt     120
agaatgaata agaagggact tactgtgcta tttatagcga taatgctcct ttcagtagtt     180
ccagtgcact ttgtgtccgc agaaacacca ccggttagtt cagaaaattc aacaacttct     240
atactcccta accaacaagt tgtgacaaaa gaagtttcac aagcggcgct taatgctata     300
atgaaaggac aacccaacat ggttcttata atcaagacta aggaaggcaa acttgaagag     360
gcaaaaaccg agcttgaaaa gctaggtgca gagattcttg acgaaaatag agttcttaac     420
atgttgctag ttaagattaa gcctgagaaa gttaagagc tcaactatat ctcatctctt      480
gaaaaagcct ggcttaacag agaagttaag ctttcccctc caattgtcga aaaggacgtc     540
aagactaagg agccctccct agaaccaaaa atgtataaca gcacctgggt aattaatgct     600
ctccagttca tccaggaatt tggatatgat ggtagtggtg ttgttgttgc agtacttgac     660
```

```
acgggagttg atccgaacca tcctttcttg agcataactc cagatggacg caggaaaatt    720
atagaatgga aggattttac agacgaggga ttcgtggata catcattcag ctttagcaag    780
gttgtaaatg ggactcttat aattaacaca acattccaag tggcctcagg tctcacgctg    840
aatgaatcga caggacttat ggaatacgtt gttaagactg tttacgtgag caatgtgacc    900
attggaaata tcacttctgc taatggcatc tatcacttcg gcctgctccc agaaagatac    960
ttcgacttaa acttcgatgg tgatcaagag gacttctatc ctgtcttatt agttaactcc   1020
actggcaatg gttatgacat tgcatatgtg gatactgacc ttgactacga cttcaccgac   1080
gaagttccac ttggccagta caacgttact tatgatgttg ctgttttttag ctactactac   1140
ggtcctctca actacgtgct tgcagaaata gatcctaacg gagaatatgc agtatttggg   1200
tgggatggtc acggtcacgg aactcacgta gctggaactg ttgctggtta cgacagcaac   1260
aatgatgctt gggattggct cagtatgtac tctggtgaat gggaagtgtt ctcaagactc   1320
tatggttggg attatacgaa cgttaccaca gacaccgtgc agggtgttgc tccaggtgcc   1380
caaataatgg caataagagt tcttaggagt gatggacggg gtagcatgtg ggatattata   1440
gaaggtatga catacgcagc aacccatggt gcagacgtta taagcatgag tctcggtgga   1500
aatgctccat acttagatgg tactgatcca gaaagcgttg ctgtggatga gcttaccgaa   1560
aagtacggtg ttgtattcgt aatagctgca ggaaatgaag gtcctggcat taacatcgtt   1620
ggaagtcctg tgttgcaac aaaggcaata actgttggag ctgctgcagt gcccattaac   1680
gttggagttt atgttcccca agcacttgga tatcctgatt actatggatt ctattacttc   1740
cccgcctaca caaacgttag aatagcattc ttctcaagca gagggccgag aatagatggt   1800
gaaataaaac ccaatgtagt ggctccaggt tacggaattt actcatccct gccgatgtgg   1860
attggcggag ctgacttcat gtctggaact tcgatggcta ctccacatgt cagcggtgtc   1920
gttgcactcc tcataagcgg ggcaaaggcc gagggaatat actacaatcc agatataatt   1980
aagaaggttc ttgagagcgg tgcaacctgg cttgagggag atccatatac tgggcagaag   2040
tacactgagc ttgaccaagg tcatggtctt gttaacgtta ccaagtcctg ggaaatcctt   2100
aaggctataa acggcaccac tctcccaatt gttgatcact gggcagacaa gtcctacagc   2160
gactttgcgg agtacttggg tgtggacgtt ataagaggtc tctacgcaag gaactctata   2220
cctgacattg tcgagtggca cattaagtac gtaggggaca cggagtacag aactttttgag   2280
atctatgcaa ctgagccatg gattaagcct tttgtcagtg gaagtgtaat tctagagaac   2340
aataccgagt ttgtccttag ggtgaaatat gatgtagagg gtcttgagcc aggtctctat   2400
gttggaagga taatcattga tgatccaaca acgccagtta ttgaagacga gatcttgaac   2460
acaattgtta ttcccgagaa gttcactcct gagaacaatt acaccctcac ctggtatgat   2520
attaatggtc cagaaatggt gactcaccac ttcttcactg tgcctgaggg agtggacgtt   2580
ctctacgcga tgaccacata ctgggactac ggtctgtaca gaccagatgg aatgtttgtg   2640
ttcccatacc agctagatta tcttcccgct gcagtctcaa atccaatgcc tggaaactgg   2700
gagctagtat ggactggatt taactttgca cccctctatg agtcgggctt ccttgtaagg   2760
atttacggag tagagataac tccaagcgtt tggtacatta acaggacata ccttgacact   2820
aacactgaat tctcaattga attcaatatt actaacatct atgccccaat taatgcaact   2880
ctaatcccca ttggccttgg aacctacaat gcgagcgttg aaagcgttgg tgatgggagt   2940
ttcttcataa agggcattga agttcctgaa ggcaccgcag agttgaagat taggataggc   3000
```

-continued

```
aacccaagtg ttccgaattc agatctagac ttgtaccttt atgacagtaa aggcaattta    3060
gtggccttag atggaaaccc aacagcagaa gaagaggttg tagttgagta tcctaagcct    3120
ggagtttatt caatagtagt acatggttac agcgtcaggg acgaaaatgg taatccaacg    3180
acaaccacct ttgacttagt tgttcaaatg acccttgata atggaaacat aaagcttgac    3240
aaagactcga ttattcttgg aagcaatgaa agcgtagttg taactgcaaa cataacaatt    3300
gatagagatc atcctacagg agtatactct ggtatcatag agattagaga taatgaggtc    3360
taccaggata caaatacttc aattgcgaaa atacccataa cttttggtaat tgacaaggcg    3420 gactttgccg ttggtctcac accagcagag ggagtacttg gagaggctag aaattacact    3480
ctaattgtaa agcatgccct aacactagag cctgtgccaa atgctacagt gattatagga    3540
aactacacct acctcacaga cgaaaacggt acagtgacat tcacgtatgc tccaactaag    3600
ttaggcagtg atgaaatcac agtcatagtt aagaaagaga acttcaacac attagagaag    3660
accttccaaa tcacagtatc agagcctgaa ataactgaag aggacataaa tgagcccaag    3720
cttgcaatgt catcaccaga agcaaatgct accatagtat cagttgagat ggagagtgag    3780
ggtggcgtta aaagacagt gacagtggaa ataactataa acggaaccgc taatgagact    3840
gcaacaatag tggttcctgt tcctaagaag gccgaaaaca tcgaggtaag tggagaccac    3900
gtaatttcct atagtataga ggaaggagag tacgccaagt acgttataat tacagtgaag    3960
tttgcatcac ctgtaacagt aactgttact tacactatct atgctggccc aagagtctca    4020
atcttgacac ttaacttcct tggctactca tggtacagac tatattcaca gaagtttgac    4080
gaattgtacc aaaaggccct tgaattggga gtggacaacg agacattagc tttagccctc    4140
agctaccatg aaaaagccaa agagtactac gaaaaggccc ttgagcttag cgagggtaac    4200
ataatccaat accttggaga cataagacta ttacctccat aagacaggc atacatcaat    4260 gaaatgaagg cagttaagat actggaaaag gccatagaaa aattagaggg tgaagagtaa    4320
tctccaattt ttcccacttt ttcttttata acattccaag ccttttctta gcttcttcgc    4380
tcattctatc aggagtccat ggaggatcaa aggtaagttc aacctccaca tctcttactc    4440
ctgggatttc gagtactttc tcctctacag ctctaagaag ccagagagtt aaaggacacc    4500
caggagttgt cattgtcatc tttatatata ccgttttgtc aggattaatc tttagctcat    4560
aaattaatcc aaggtttaca acatccatcc caatttctgg gtcgataacc tcctttagct    4620
tttccagaat catttcttca gtaatttcaa ggttctcatc tttggtttct ctcacaaacc    4680
caatttcaac ctgcctgata ccttctaact ccctaagctt gttatatatc tccaaaagag    4740
tggcatcatc aattttctct ttaaa                                          4765
```

<210> SEQ ID NO 6
<211> LENGTH: 1398
<212> TYPE: PRT
<213> ORGANISM: Pyrococcus furiosus

<400> SEQUENCE: 6

```
Met Asn Lys Lys Gly Leu Thr Val Leu Phe Ile Ala Ile Met Leu Leu
1               5                   10                  15

Ser Val Val Pro Val His Phe Val Ser Ala Glu Thr Pro Pro Val Ser
            20                  25                  30

Ser Glu Asn Ser Thr Thr Ser Ile Leu Pro Asn Gln Gln Val Val Thr
        35                  40                  45

Lys Glu Val Ser Gln Ala Ala Leu Asn Ala Ile Met Lys Gly Gln Pro
    50                  55                  60
```

```
Asn Met Val Leu Ile Ile Lys Thr Lys Glu Gly Lys Leu Glu Glu Ala
65                  70                  75                  80

Lys Thr Glu Leu Glu Lys Leu Gly Ala Glu Ile Leu Asp Glu Asn Arg
            85                  90                  95

Val Leu Asn Met Leu Leu Val Lys Ile Lys Pro Glu Lys Val Lys Glu
                100                 105                 110

Leu Asn Tyr Ile Ser Ser Leu Glu Lys Ala Trp Leu Asn Arg Glu Val
            115                 120                 125

Lys Leu Ser Pro Pro Ile Val Glu Lys Asp Val Lys Thr Lys Glu Pro
130                 135                 140

Ser Leu Glu Pro Lys Met Tyr Asn Ser Thr Trp Val Ile Asn Ala Leu
145                 150                 155                 160

Gln Phe Ile Gln Glu Phe Gly Tyr Asp Gly Ser Gly Val Val Val Ala
                165                 170                 175

Val Leu Asp Thr Gly Val Asp Pro Asn His Pro Phe Leu Ser Ile Thr
            180                 185                 190

Pro Asp Gly Arg Arg Lys Ile Ile Glu Trp Lys Asp Phe Thr Asp Glu
            195                 200                 205

Gly Phe Val Asp Thr Ser Phe Ser Phe Ser Lys Val Val Asn Gly Thr
            210                 215                 220

Leu Ile Ile Asn Thr Thr Phe Gln Val Ala Ser Gly Leu Thr Leu Asn
225                 230                 235                 240

Glu Ser Thr Gly Leu Met Glu Tyr Val Val Lys Thr Val Tyr Val Ser
                245                 250                 255

Asn Val Thr Ile Gly Asn Ile Thr Ser Ala Asn Gly Ile Tyr His Phe
            260                 265                 270

Gly Leu Leu Pro Glu Arg Tyr Phe Asp Leu Asn Phe Asp Gly Asp Gln
            275                 280                 285

Glu Asp Phe Tyr Pro Val Leu Leu Val Asn Ser Thr Gly Asn Gly Tyr
            290                 295                 300

Asp Ile Ala Tyr Val Asp Thr Asp Leu Asp Tyr Asp Phe Thr Asp Glu
305                 310                 315                 320

Val Pro Leu Gly Gln Tyr Asn Val Thr Tyr Asp Val Ala Val Phe Ser
                325                 330                 335

Tyr Tyr Tyr Gly Pro Leu Asn Tyr Val Leu Ala Glu Ile Asp Pro Asn
                340                 345                 350

Gly Glu Tyr Ala Val Phe Gly Trp Asp Gly His Gly His Gly Thr His
            355                 360                 365

Val Ala Gly Thr Val Ala Gly Tyr Asp Ser Asn Asn Asp Ala Trp Asp
            370                 375                 380

Trp Leu Ser Met Tyr Ser Gly Glu Trp Glu Val Phe Ser Arg Leu Tyr
385                 390                 395                 400

Gly Trp Asp Tyr Thr Asn Val Thr Thr Asp Thr Val Gln Gly Val Ala
                405                 410                 415

Pro Gly Ala Gln Ile Met Ala Ile Arg Val Leu Arg Ser Asp Gly Arg
            420                 425                 430

Gly Ser Met Trp Asp Ile Ile Glu Gly Met Thr Tyr Ala Ala Thr His
            435                 440                 445

Gly Ala Asp Val Ile Ser Met Ser Leu Gly Gly Asn Ala Pro Tyr Leu
            450                 455                 460

Asp Gly Thr Asp Pro Glu Ser Val Ala Val Asp Glu Leu Thr Glu Lys
465                 470                 475                 480
```

-continued

```
Tyr Gly Val Val Phe Val Ile Ala Ala Gly Asn Glu Gly Pro Gly Ile
                485                 490                 495

Asn Ile Val Gly Ser Pro Gly Val Ala Thr Lys Ala Ile Thr Val Gly
            500                 505                 510

Ala Ala Ala Val Pro Ile Asn Val Gly Val Tyr Val Ser Gln Ala Leu
            515                 520                 525

Gly Tyr Pro Asp Tyr Tyr Gly Phe Tyr Tyr Phe Pro Ala Tyr Thr Asn
        530                 535                 540

Val Arg Ile Ala Phe Phe Ser Ser Arg Gly Pro Arg Ile Asp Gly Glu
545                 550                 555                 560

Ile Lys Pro Asn Val Val Ala Pro Gly Tyr Gly Ile Tyr Ser Ser Leu
                565                 570                 575

Pro Met Trp Ile Gly Gly Ala Asp Phe Met Ser Gly Thr Ser Met Ala
            580                 585                 590

Thr Pro His Val Ser Gly Val Val Ala Leu Leu Ile Ser Gly Ala Lys
            595                 600                 605

Ala Glu Gly Ile Tyr Tyr Asn Pro Asp Ile Ile Lys Lys Val Leu Glu
        610                 615                 620

Ser Gly Ala Thr Trp Leu Glu Gly Asp Pro Tyr Thr Gly Gln Lys Tyr
625                 630                 635                 640

Thr Glu Leu Asp Gln Gly His Gly Leu Val Asn Val Thr Lys Ser Trp
                645                 650                 655

Glu Ile Leu Lys Ala Ile Asn Gly Thr Thr Leu Pro Ile Val Asp His
            660                 665                 670

Trp Ala Asp Lys Ser Tyr Ser Asp Phe Ala Glu Tyr Leu Gly Val Asp
        675                 680                 685

Val Ile Arg Gly Leu Tyr Ala Arg Asn Ser Ile Pro Asp Ile Val Glu
690                 695                 700

Trp His Ile Lys Tyr Val Gly Asp Thr Glu Tyr Arg Thr Phe Glu Ile
705                 710                 715                 720

Tyr Ala Thr Glu Pro Trp Ile Lys Pro Phe Val Ser Gly Ser Val Ile
                725                 730                 735

Leu Glu Asn Asn Thr Glu Phe Val Leu Arg Val Lys Tyr Asp Val Glu
            740                 745                 750

Gly Leu Glu Pro Gly Leu Tyr Val Gly Arg Ile Ile Asp Asp Pro
        755                 760                 765

Thr Thr Pro Val Ile Glu Asp Glu Ile Leu Asn Thr Ile Val Ile Pro
770                 775                 780

Glu Lys Phe Thr Pro Glu Asn Asn Tyr Thr Leu Thr Trp Tyr Asp Ile
785                 790                 795                 800

Asn Gly Pro Glu Met Val Thr His His Phe Thr Val Pro Glu Gly
                805                 810                 815

Val Asp Val Leu Tyr Ala Met Thr Thr Tyr Trp Asp Tyr Gly Leu Tyr
            820                 825                 830

Arg Pro Asp Gly Met Phe Val Phe Pro Tyr Gln Leu Asp Tyr Leu Pro
        835                 840                 845

Ala Ala Val Ser Asn Pro Met Pro Gly Asn Trp Glu Leu Val Trp Thr
850                 855                 860

Gly Phe Asn Phe Ala Pro Leu Tyr Glu Ser Gly Phe Leu Val Arg Ile
865                 870                 875                 880

Tyr Gly Val Glu Ile Thr Pro Ser Val Trp Tyr Ile Asn Arg Thr Tyr
                885                 890                 895

Leu Asp Thr Asn Thr Glu Phe Ser Ile Glu Phe Asn Ile Thr Asn Ile
```

-continued

```
                900                 905                 910
Tyr Ala Pro Ile Asn Ala Thr Leu Ile Pro Ile Gly Leu Gly Thr Tyr
        915                 920                 925

Asn Ala Ser Val Glu Ser Val Gly Asp Gly Phe Phe Ile Lys Gly
    930                 935                 940

Ile Glu Val Pro Glu Gly Thr Ala Glu Leu Lys Ile Arg Ile Gly Asn
945                 950                 955                 960

Pro Ser Val Pro Asn Ser Asp Leu Asp Leu Tyr Leu Tyr Asp Ser Lys
                965                 970                 975

Gly Asn Leu Val Ala Leu Asp Gly Asn Pro Thr Ala Glu Glu Val
            980                 985                 990

Val Val Glu Tyr Pro Lys Pro Gly Val Tyr Ser Ile Val Val His Gly
        995                 1000                1005

Tyr Ser Val Arg Asp Glu Asn Gly Asn Pro Thr Thr Thr Thr Phe
1010                1015                1020

Asp Leu Val Val Gln Met Thr Leu Asp Asn Gly Asn Ile Lys Leu
1025                1030                1035

Asp Lys Asp Ser Ile Ile Leu Gly Ser Asn Glu Ser Val Val Val
1040                1045                1050

Thr Ala Asn Ile Thr Ile Asp Arg Asp His Pro Thr Gly Val Tyr
1055                1060                1065

Ser Gly Ile Ile Glu Ile Arg Asp Asn Glu Val Tyr Gln Asp Thr
1070                1075                1080

Asn Thr Ser Ile Ala Lys Ile Pro Ile Thr Leu Val Ile Asp Lys
1085                1090                1095

Ala Asp Phe Ala Val Gly Leu Thr Pro Ala Glu Gly Val Leu Gly
1100                1105                1110

Glu Ala Arg Asn Tyr Thr Leu Ile Val Lys His Ala Leu Thr Leu
1115                1120                1125

Glu Pro Val Pro Asn Ala Thr Val Ile Gly Asn Tyr Thr Tyr
1130                1135                1140

Leu Thr Asp Glu Asn Gly Thr Val Thr Phe Thr Tyr Ala Pro Thr
1145                1150                1155

Lys Leu Gly Ser Asp Glu Ile Thr Val Ile Val Lys Lys Glu Asn
1160                1165                1170

Phe Asn Thr Leu Glu Lys Thr Phe Gln Ile Thr Val Ser Glu Pro
1175                1180                1185

Glu Ile Thr Glu Glu Asp Ile Asn Glu Pro Lys Leu Ala Met Ser
1190                1195                1200

Ser Pro Glu Ala Asn Ala Thr Ile Val Ser Val Glu Met Glu Ser
1205                1210                1215

Glu Gly Gly Val Lys Lys Thr Val Thr Val Glu Ile Thr Ile Asn
1220                1225                1230

Gly Thr Ala Asn Glu Thr Ala Thr Ile Val Val Pro Val Pro Lys
1235                1240                1245

Lys Ala Glu Asn Ile Glu Val Ser Gly Asp His Val Ile Ser Tyr
1250                1255                1260

Ser Ile Glu Glu Gly Glu Tyr Ala Lys Tyr Val Ile Ile Thr Val
1265                1270                1275

Lys Phe Ala Ser Pro Val Thr Val Thr Tyr Thr Ile Tyr
1280                1285                1290

Ala Gly Pro Arg Val Ser Ile Leu Thr Leu Asn Phe Leu Gly Tyr
1295                1300                1305
```

```
Ser Trp Tyr Arg Leu Tyr Ser Gln Lys Phe Asp Glu Leu Tyr Gln
    1310                1315                1320

Lys Ala Leu Glu Leu Gly Val Asp Asn Glu Thr Leu Ala Leu Ala
    1325                1330                1335

Leu Ser Tyr His Glu Lys Ala Lys Glu Tyr Tyr Glu Lys Ala Leu
    1340                1345                1350

Glu Leu Ser Glu Gly Asn Ile Ile Gln Tyr Leu Gly Asp Ile Arg
    1355                1360                1365

Leu Leu Pro Pro Leu Arg Gln Ala Tyr Ile Asn Glu Met Lys Ala
    1370                1375                1380

Val Lys Ile Leu Glu Lys Ala Ile Glu Glu Leu Glu Gly Glu Glu
    1385                1390                1395
```

<210> SEQ ID NO 7
<211> LENGTH: 35
<212> TYPE: DNA
<213> ORGANISM: Artificial Sequence
<220> FEATURE:
<223> OTHER INFORMATION: Synthetic

<400> SEQUENCE: 7
ggwwsdrrtg ttrrhgthgc dgtdmtygac acbgg                       35

<210> SEQ ID NO 8
<211> LENGTH: 32
<212> TYPE: DNA
<213> ORGANISM: Artificial Sequence
<220> FEATURE:
<223> OTHER INFORMATION: Synthetic

<400> SEQUENCE: 8
kstcacggaa ctcacgtdgc bgghacdgtt gc                          32

<210> SEQ ID NO 9
<211> LENGTH: 33
<212> TYPE: DNA
<213> ORGANISM: Artificial Sequence
<220> FEATURE:
<223> OTHER INFORMATION: Synthetic

<400> SEQUENCE: 9
ascmgcaach gtkccvgcha cgtgagttcc gtg                         33

<210> SEQ ID NO 10
<211> LENGTH: 34
<212> TYPE: DNA
<213> ORGANISM: Artificial Sequence
<220> FEATURE:
<223> OTHER INFORMATION: Synthetic

<400> SEQUENCE: 10
chccgsyvac rtgbggagwd gccatbgavg tdcc                        34

<210> SEQ ID NO 11
<211> LENGTH: 1977
<212> TYPE: DNA
<213> ORGANISM: Artificial Sequence
<220> FEATURE:
<223> OTHER INFORMATION: Synthetic

<400> SEQUENCE: 11
atgaagaggt taggtgctgt ggtgctggca ctggtgctcg tgggtcttct ggccggaacg    60

```
gcccttgcgg cacccgtaaa accggttgtc aggaacaacg cggttcagca gaagaactac    120
ggactgctga ccccgggact gttcaagaaa gtccagagga tgaactggaa ccaggaagtg    180
gacaccgtca taatgttcgg gagctacgga gacagggaca gggcggttaa ggtactgagg    240
ctcatgggcg cccaggtcaa gtactcctac aagataatcc ctgctgtcgc ggttaaaata    300
aaggccaggg accttctgct gatcgcgggc atgatagaca cgggttactt cggtaacaca    360
agggtctcgg gcataaagtt catacaggag gattacaagg ttcaggttga cgacgccact    420
tccgtctccc agatagggggc cgataccgtc tggaactccc tcggctacga cggaagcggt    480
gtggtggttg ccatcgtcga tacgggtata gacgcgaacc accccgatct gaagggcaag    540
gtcataggct ggtacgacgc cgtcaacggc aggtcgaccc cctacgatga ccagggacac    600
ggaacccacg ttgcgggtat cgttgccgga accggcagcg ttaactccca gtacataggc    660
gtcgcccccg gcgcgaagct cgtcggcgtc aaggttctcg gtgccgacgg ttcgggaagc    720
gtctccacca tcatcgcggg tgttgactgg gtcgtccaga caaggacaa gtacgggata    780 agggtcatca acctctccct cggctcctcc cagagctccg acggaaccga ctccctcagt    840
caggccgtca caacgccctg ggacgccggt atagtagtct gcgtcgccgc cggcaacagc    900
gggccgaaca cctacaccgt cggctcaccc gccgccgcga gcaaggtcat aaccgtcggt    960
gcagttgaca gcaacgacaa catcgccagc ttctccagcg ggggaccgac cgcggacgga   1020
aggctcaagc cggaagtcgt cgcccccggc gttgacatca tagcccccgcg cgccagcgga   1080 accagcatgg gcaccccgat aaacgactac tacaccaagg cctctggaac cagcatggcc   1140
accccgcacg tttcgggcgt tggcgcgctc atcctccagg cccacccgag ctggaccccg   1200
gacaaggtga agaccgccct catcgagacc gccgacatag tcgcccccaa ggagatagcg   1260
gacatcgcct acgtgcgggt agggtgaac gtctacaagg ccatcaagta cgacgactac   1320
gccaagctca ccttcaccgg ctccgtcgcc gacaagggaa cgccaccca caccttcgac   1380 gtcagcggcg ccaccttcgt gaccgccacc ctctactggg acacgggctc gagcgacatc   1440
gacctctacc tctacgaccc caacgggaac gaggttgact actcctacac cgcctactac   1500
ggcttcgaga aggtcggcta ctacaacccg accgccggaa cctggacggt caaggtcgtc   1560
agctacaagg gcgcggcgaa ctaccaggtc gacgtcgtca cgacgggag cctcagccag   1620 tccggcggcg gcaacccgaa tccaaacccc aacccgaacc caacccccgac caccgacacc   1680 cagaccttca ccggttccgt taacgactac tgggacacca cgacaccctt caccatgaac   1740
gtcaacagcg gtgccaccaa gataaccggt gacctgacct tcgatacttc ctacaacgac   1800
ctcgacctct acctctacga ccccaacggc aacctcgttg acaggtccac gtcgagcaac   1860
agctacgagc acgtcgagta cgccaacccc gccccgggaa cctggacgtt cctcgtctac   1920
gcctacagca cctacggctg gcggactac cagctcaagg ccgtcgtcta ctacggg       1977
```

<210> SEQ ID NO 12
<211> LENGTH: 659
<212> TYPE: PRT
<213> ORGANISM: Thermococcus celer

<400> SEQUENCE: 12

Met Lys Arg Leu Gly Ala Val Val Leu Ala Leu Val Leu Val Gly Leu
1               5                   10                  15

Leu Ala Gly Thr Ala Leu Ala Ala Pro Val Lys Pro Val Val Arg Asn
            20                  25                  30

Asn Ala Val Gln Gln Lys Asn Tyr Gly Leu Leu Thr Pro Gly Leu Phe

-continued

```
                35                  40                  45
Lys Lys Val Gln Arg Met Asn Trp Asn Gln Glu Val Asp Thr Val Ile
    50                  55                  60
Met Phe Gly Ser Tyr Gly Asp Arg Asp Arg Ala Val Lys Val Leu Arg
65                  70                  75                  80
Leu Met Gly Ala Gln Val Lys Tyr Ser Tyr Lys Ile Ile Pro Ala Val
                85                  90                  95
Ala Val Lys Ile Lys Ala Arg Asp Leu Leu Ile Ala Gly Met Ile
                100                 105                 110
Asp Thr Gly Tyr Phe Gly Asn Thr Arg Val Ser Gly Ile Lys Phe Ile
                115                 120                 125
Gln Glu Asp Tyr Lys Val Gln Val Asp Ala Thr Ser Val Ser Gln
    130                 135                 140
Ile Gly Ala Asp Thr Val Trp Asn Ser Leu Gly Tyr Asp Gly Ser Gly
145                 150                 155                 160
Val Val Val Ala Ile Val Asp Thr Gly Ile Asp Ala Asn His Pro Asp
                165                 170                 175
Leu Lys Gly Lys Val Ile Gly Trp Tyr Asp Ala Val Asn Gly Arg Ser
                180                 185                 190
Thr Pro Tyr Asp Asp Gln Gly His Gly Thr His Val Ala Gly Ile Val
                195                 200                 205
Ala Gly Thr Gly Ser Val Asn Ser Gln Tyr Ile Gly Val Ala Pro Gly
    210                 215                 220
Ala Lys Leu Val Gly Val Lys Val Leu Gly Ala Asp Gly Ser Gly Ser
225                 230                 235                 240
Val Ser Thr Ile Ile Ala Gly Val Asp Trp Val Val Gln Asn Lys Asp
                245                 250                 255
Lys Tyr Gly Ile Arg Val Ile Asn Leu Ser Leu Gly Ser Ser Gln Ser
                260                 265                 270
Ser Asp Gly Thr Asp Ser Leu Ser Gln Ala Val Asn Asn Ala Trp Asp
    275                 280                 285
Ala Gly Ile Val Val Cys Val Ala Ala Gly Asn Ser Gly Pro Asn Thr
    290                 295                 300
Tyr Thr Val Gly Ser Pro Ala Ala Ser Lys Val Ile Thr Val Gly
305                 310                 315                 320
Ala Val Asp Ser Asn Asp Asn Ile Ala Ser Phe Ser Ser Arg Gly Pro
                325                 330                 335
Thr Ala Asp Gly Arg Leu Lys Pro Glu Val Val Ala Pro Gly Val Asp
                340                 345                 350
Ile Ile Ala Pro Arg Ala Ser Gly Thr Ser Met Gly Thr Pro Ile Asn
                355                 360                 365
Asp Tyr Tyr Thr Lys Ala Ser Gly Thr Ser Met Ala Thr Pro His Val
    370                 375                 380
Ser Gly Val Gly Ala Leu Ile Leu Gln Ala His Pro Ser Trp Thr Pro
385                 390                 395                 400
Asp Lys Val Lys Thr Ala Leu Ile Glu Thr Ala Asp Ile Val Ala Pro
                405                 410                 415
Lys Glu Ile Ala Asp Ile Ala Tyr Gly Ala Gly Arg Val Asn Val Tyr
                420                 425                 430
Lys Ala Ile Lys Tyr Asp Asp Tyr Ala Lys Leu Thr Phe Thr Gly Ser
                435                 440                 445
Val Ala Asp Lys Gly Ser Ala Thr His Thr Phe Asp Val Ser Gly Ala
    450                 455                 460
```

```
Thr Phe Val Thr Ala Thr Leu Tyr Trp Asp Thr Gly Ser Ser Asp Ile
465                 470                 475                 480

Asp Leu Tyr Leu Tyr Asp Pro Asn Gly Asn Glu Val Asp Tyr Ser Tyr
            485                 490                 495

Thr Ala Tyr Tyr Gly Phe Glu Lys Val Gly Tyr Tyr Asn Pro Thr Ala
        500                 505                 510

Gly Thr Trp Thr Val Lys Val Ser Tyr Lys Gly Ala Ala Asn Tyr
        515                 520                 525

Gln Val Asp Val Ser Asp Gly Ser Leu Ser Gln Ser Gly Gly Gly
    530                 535                 540

Asn Pro Asn Pro Asn Pro Asn Pro Asn Pro Thr Pro Thr Thr Asp Thr
545                 550                 555                 560

Gln Thr Phe Thr Gly Ser Val Asn Asp Tyr Trp Asp Thr Ser Asp Thr
            565                 570                 575

Phe Thr Met Asn Val Asn Ser Gly Ala Thr Lys Ile Thr Gly Asp Leu
            580                 585                 590

Thr Phe Asp Thr Ser Tyr Asn Asp Leu Asp Leu Tyr Leu Tyr Asp Pro
        595                 600                 605

Asn Gly Asn Leu Val Asp Arg Ser Thr Ser Ser Asn Ser Tyr Glu His
610                 615                 620

Val Glu Tyr Ala Asn Pro Ala Pro Gly Thr Trp Thr Phe Leu Val Tyr
625                 630                 635                 640

Ala Tyr Ser Thr Tyr Gly Trp Ala Asp Tyr Gln Leu Lys Ala Val Val
            645                 650                 655

Tyr Tyr Gly

<210> SEQ ID NO 13
<211> LENGTH: 28
<212> TYPE: DNA
<213> ORGANISM: Artificial Sequence
<220> FEATURE:
<223> OTHER INFORMATION: Synthetic

<400> SEQUENCE: 13
agagggatcc atgaaggggc tgaaagct                                              28

<210> SEQ ID NO 14
<211> LENGTH: 30
<212> TYPE: DNA
<213> ORGANISM: Artificial Sequence
<220> FEATURE:
<223> OTHER INFORMATION: Synthetic

<400> SEQUENCE: 14
agaggcatgc gctctagact ctgggagagt                                            30

<210> SEQ ID NO 15
<211> LENGTH: 1962
<212> TYPE: DNA
<213> ORGANISM: Artificial Sequence
<220> FEATURE:
<223> OTHER INFORMATION: Synthetic

<400> SEQUENCE: 15
atgaaggggc tgaaagctct catattagtg attttagttc taggtttggt agtagggagc           60
gtagcggcag ctccagagaa gaaagttgaa caagtaagaa atgttgagaa gaactatggt          120
ctgctaacgc caggactgtt cagaaaaatt caaaaattga atcctaacga ggaaatcagc          180
```

-continued

```
acagtaattg tatttgaaaa ccatagggaa aagaaattg cagtaagagt tcttgagtta      240
atgggtgcaa aagttaggta tgtgtaccat attatacccg caatagctgc cgatcttaag    300
gttagagact tactagtcat ctcaggttta cagggggta aagctaagct ttcaggtgtt      360
aggtttatcc aggaagacta caaagttaca gtttcagcag aattagaagg actggatgag    420
tctgcagctc aagttatggc aacttacgtt tggaacttgg gatatgatgg ttctggaatc    480
acaataggaa taattgacac tggaattgac gcttctcatc cagatctcca aggaaaagta    540
attgggtggg tagattttgt caatggtagg agttatccat acgatgacca tggacatgga    600
actcatgtag cttcaatagc agctggtact ggagcagcaa gtaatggcaa gtacaaggga    660
atggctccag gagctaagct ggcgggaatt aaggttctag gtgccgatgg ttctggaagc    720
atatctacta taattaaggg agttgagtgg gccgttgata caaagataa gtacggaatt     780
aaggtcatta atctttctct tggttcaagc cagagctcag atggtactga cgctctaagt    840
caggctgtta atgcagcgtg ggatgctgga ttagttgttg tggttgccgc tggaaacagt    900
ggacctaaca agtatacaat cggttctcca gcagctgcaa gcaaagttat tacagttgga    960
gccgttgaca agtatgatgt tataacaagc ttctcaagca gagggccaac tgcagacggc   1020
aggcttaagc ctgaggttgt tgctccagga aactggataa ttgctgccag agcaagtgga   1080
actagcatgg gtcaaccaat taatgactat tacacagcag ctcctgggac atcaatggca   1140
actcctcacg tagctggtat tgcagccctc ttgctccaag cacacccgag ctggactcca   1200
gacaaagtaa aaacagccct catagaaact gctgatatcg taaagccaga tgaaatagcc   1260
gatatagcct acgtgcagg tagggttaat gcatacaagg ctataaacta cgataactat    1320
gcaaagctag tgttcactgg atatgttgcc aacaaaggca gccaaactca ccagttcgtt   1380
attagcggag cttcgttcgt aactgccaca ttatactggg acaatgccaa tagcgaccct   1440
gatctttacc tctacgatcc caatggaaac caggttgact actcttacac cgcctactat   1500
ggattcgaaa aggttggtta ttacaaccca actgatggaa catggacaat taaggttgta   1560
agctacagcg gaagtgcaaa ctatcaagta gatgtggtaa gtgatggttc cctttcacag   1620
cctggaagtt caccatctcc acaaccagaa ccaacagtag acgcaaagac gttccaagga   1680
tccgatcact actactatga caggagcgac accttacaa tgaccgttaa ctctggggct    1740
acaaagatta ctggagacct agtgtttgac acaagctacc atgatcttga cctttacctc   1800
tacgatccta accagaagct tgtagataga tcggagagtc ccaacagcta cgaacacgta   1860
gaatacttaa ccccgcccc aggaacctgg tacttcctag tatatgccta ctacacttac   1920
ggttgggctt actacgagct gacggctaaa gtttattatg gc                      1962
```

<210> SEQ ID NO 16
<211> LENGTH: 654
<212> TYPE: PRT
<213> ORGANISM: Pyrococcus furiosus

<400> SEQUENCE: 16

```
Met Lys Gly Leu Lys Ala Leu Ile Leu Val Ile Leu Val Leu Gly Leu
1               5                   10                  15

Val Val Gly Ser Val Ala Ala Ala Pro Glu Lys Lys Val Glu Gln Val
            20                  25                  30

Arg Asn Val Glu Lys Asn Tyr Gly Leu Leu Thr Pro Gly Leu Phe Arg
        35                  40                  45

Lys Ile Gln Lys Leu Asn Pro Asn Glu Glu Ile Ser Thr Val Ile Val
    50                  55                  60
```

```
Phe Glu Asn His Arg Glu Lys Glu Ile Ala Val Arg Val Leu Glu Leu
 65                  70                  75                  80
Met Gly Ala Lys Val Arg Tyr Val Tyr His Ile Ile Pro Ala Ile Ala
                 85                  90                  95
Ala Asp Leu Lys Val Arg Asp Leu Leu Val Ile Ser Gly Leu Thr Gly
                100                 105                 110
Gly Lys Ala Lys Leu Ser Gly Val Arg Phe Ile Gln Glu Asp Tyr Lys
                115                 120                 125
Val Thr Val Ser Ala Glu Leu Glu Gly Leu Asp Glu Ser Ala Ala Gln
    130                 135                 140
Val Met Ala Thr Tyr Val Trp Asn Leu Gly Tyr Asp Gly Ser Gly Ile
145                 150                 155                 160
Thr Ile Gly Ile Ile Asp Thr Gly Ile Asp Ala Ser His Pro Asp Leu
                165                 170                 175
Gln Gly Lys Val Ile Gly Trp Val Asp Phe Val Asn Gly Arg Ser Tyr
                180                 185                 190
Pro Tyr Asp Asp His Gly His Gly Thr His Val Ala Ser Ile Ala Ala
    195                 200                 205
Gly Thr Gly Ala Ala Ser Asn Gly Lys Tyr Lys Gly Met Ala Pro Gly
    210                 215                 220
Ala Lys Leu Ala Gly Ile Lys Val Leu Gly Ala Asp Gly Ser Gly Ser
225                 230                 235                 240
Ile Ser Thr Ile Ile Lys Gly Val Glu Trp Ala Val Asp Asn Lys Asp
                245                 250                 255
Lys Tyr Gly Ile Lys Val Ile Asn Leu Ser Leu Gly Ser Ser Gln Ser
                260                 265                 270
Ser Asp Gly Thr Asp Ala Leu Ser Gln Ala Val Asn Ala Ala Trp Asp
    275                 280                 285
Ala Gly Leu Val Val Val Ala Ala Gly Asn Ser Gly Pro Asn Lys
    290                 295                 300
Tyr Thr Ile Gly Ser Pro Ala Ala Ser Lys Val Ile Thr Val Gly
305                 310                 315                 320
Ala Val Asp Lys Tyr Asp Val Ile Thr Ser Phe Ser Ser Arg Gly Pro
                325                 330                 335
Thr Ala Asp Gly Arg Leu Lys Pro Glu Val Val Ala Pro Gly Asn Trp
                340                 345                 350
Ile Ile Ala Ala Arg Ala Ser Gly Thr Ser Met Gly Gln Pro Ile Asn
    355                 360                 365
Asp Tyr Tyr Thr Ala Ala Pro Gly Thr Ser Met Ala Thr Pro His Val
    370                 375                 380
Ala Gly Ile Ala Ala Leu Leu Leu Gln Ala His Pro Ser Trp Thr Pro
385                 390                 395                 400
Asp Lys Val Lys Thr Ala Leu Ile Glu Thr Ala Asp Ile Val Lys Pro
                405                 410                 415
Asp Glu Ile Ala Asp Ile Ala Tyr Gly Ala Gly Arg Val Asn Ala Tyr
                420                 425                 430
Lys Ala Ile Asn Tyr Asp Asn Tyr Ala Lys Leu Val Phe Thr Gly Tyr
                435                 440                 445
Val Ala Asn Lys Gly Ser Gln Thr His Gln Phe Val Ile Ser Gly Ala
    450                 455                 460
Ser Phe Val Thr Ala Thr Leu Tyr Trp Asp Asn Ala Asn Ser Asp Leu
465                 470                 475                 480
```

```
Asp Leu Tyr Leu Tyr Asp Pro Asn Gly Asn Gln Val Asp Tyr Ser Tyr
                485                 490                 495

Thr Ala Tyr Tyr Gly Phe Glu Lys Val Gly Tyr Tyr Asn Pro Thr Asp
            500                 505                 510

Gly Thr Trp Thr Ile Lys Val Ser Tyr Ser Gly Ser Ala Asn Tyr
        515                 520                 525

Gln Val Asp Val Val Ser Asp Gly Ser Leu Ser Gln Pro Gly Ser Ser
    530                 535                 540

Pro Ser Pro Gln Pro Glu Pro Thr Val Asp Ala Lys Thr Phe Gln Gly
545                 550                 555                 560

Ser Asp His Tyr Tyr Tyr Asp Arg Ser Asp Thr Phe Thr Met Thr Val
                565                 570                 575

Asn Ser Gly Ala Thr Lys Ile Thr Gly Asp Leu Val Phe Asp Thr Ser
            580                 585                 590

Tyr His Asp Leu Asp Leu Tyr Leu Tyr Asp Pro Asn Gln Lys Leu Val
        595                 600                 605

Asp Arg Ser Glu Ser Pro Asn Ser Tyr Glu His Val Glu Tyr Leu Thr
    610                 615                 620

Pro Ala Pro Gly Thr Trp Tyr Phe Leu Val Tyr Ala Tyr Tyr Thr Tyr
625                 630                 635                 640

Gly Trp Ala Tyr Tyr Glu Leu Thr Ala Lys Val Tyr Tyr Gly
                645                 650
```

```
<210> SEQ ID NO 17
<211> LENGTH: 25
<212> TYPE: DNA
<213> ORGANISM: Artificial Sequence
<220> FEATURE:
<223> OTHER INFORMATION: Synthetic

<400> SEQUENCE: 17
tctgaattcg ttcttttctg tatgg                                    25

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
tgtactgctg gatccggcag                                          20

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19
agaggcatgc gtatccatca gattttgag                                30

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
```

```
agtgaacgga tacttggaac                                              20
```

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21

```
gttccaagta tccgttcact                                              20
```

<210> SEQ ID NO 22
<211> LENGTH: 12
<212> TYPE: PRT
<213> ORGANISM: Pyrococcus furiosus

<400> SEQUENCE: 22

```
Ala Glu Leu Glu Gly Leu Asp Glu Ser Ala Ala Gln
1               5                   10
```

<210> SEQ ID NO 23
<211> LENGTH: 24
<212> TYPE: DNA
<213> ORGANISM: Artificial Sequence
<220> FEATURE:
<223> OTHER INFORMATION: Synthetic

<400> SEQUENCE: 23

```
tcatggatcc accctctcct ttta                                         24
```

<210> SEQ ID NO 24
<211> LENGTH: 46
<212> TYPE: DNA
<213> ORGANISM: Artificial Sequence
<220> FEATURE:
<223> OTHER INFORMATION: Synthetic
<221> NAME/KEY: misc_feature
<222> LOCATION: (20)..(25)
<223> OTHER INFORMATION: n at postions 20-25 is a, c, g, or t.

<400> SEQUENCE: 24

```
gtctgcgcag gctgccggan nnnnnatgaa ggggctgaaa gctctc                 46
```

<210> SEQ ID NO 25
<211> LENGTH: 49
<212> TYPE: DNA
<213> ORGANISM: Artificial Sequence
<220> FEATURE:
<223> OTHER INFORMATION: Synthetic
<221> NAME/KEY: misc_feature
<222> LOCATION: (22)..(27)
<223> OTHER INFORMATION: n at postions 22-27 is a, c, g, or t.

<400> SEQUENCE: 25

```
gagagctttc agcccttca tnnnnnntcc ggcagcctgc gcagacatg               49
```

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26

```
agaggggat ccgtgagaag caaaaaa                                       27
```

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
gatgactagt aagtctctaa                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic

<400> SEQUENCE: 28
aagcctgagg ttgttgctcc                                              20

<210> SEQ ID NO 29
<211> LENGTH: 29
<212> TYPE: DNA
<213> ORGANISM: Artificial Sequence
<220> FEATURE:
<223> OTHER INFORMATION: Synthetic

<400> SEQUENCE: 29
gggcatgctc atgaacttcc aggctgtga                                    29

<210> SEQ ID NO 30
<211> LENGTH: 4
<212> TYPE: PRT
<213> ORGANISM: Artificial Sequence
<220> FEATURE:
<223> OTHER INFORMATION: Synthetic

<400> SEQUENCE: 30

Ala Gly Gly Asn
1

<210> SEQ ID NO 31
<211> LENGTH: 382
<212> TYPE: PRT
<213> ORGANISM: Bacillus subtilis

<400> SEQUENCE: 31

Met Arg Gly Lys Lys Val Trp Ile Ser Leu Leu Phe Ala Leu Ala Leu
1               5                   10                  15

Ile Phe Thr Met Ala Phe Gly Ser Thr Ser Ser Ala Gln Ala Ala Gly
                20                  25                  30

Lys Ser Asn Gly Glu Lys Lys Tyr Ile Val Gly Phe Lys Gln Thr Met
            35                  40                  45

Ser Thr Met Ser Ala Ala Lys Lys Lys Asp Val Ile Ser Glu Lys Gly
        50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Tyr Ala Gln Ser Val Pro
            100                 105                 110

Tyr Gly Val Ser Gln Ile Lys Ala Pro Ala Leu His Ser Gln Gly Tyr

```
            115                 120                 125
Thr Gly Ser Asn Val Lys Val Ala Val Ile Asp Ser Gly Ile Asp Ser
    130                 135                 140

Ser His Pro Asp Leu Lys Val Ala Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
            180                 185                 190

Pro Ser Ala Ser Leu Tyr Ala Val Lys Val Leu Gly Ala Asp Gly Ser
        195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Thr Ser Gly Ser Ser Ser Thr Val
            260                 265                 270

Gly Tyr Pro Gly Lys Tyr Pro Ser Val Ile Ala Val Gly Ala Val Asp
        275                 280                 285

Ser Ser Asn Gln Arg Ala Ser Phe Ser Ser Val Gly Pro Glu Leu Asp
    290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
            340                 345                 350

Val Arg Ser Ser Leu Glu Asn Thr Thr Thr Lys Leu Gly Asp Ser Phe
        355                 360                 365

Tyr Tyr Gly Lys Gly Leu Ile Asn Val Gln Ala Ala Ala Gln
    370                 375                 380

<210> SEQ ID NO 32
<211> LENGTH: 4
<212> TYPE: PRT
<213> ORGANISM: Artificial Sequence
<220> FEATURE:
<223> OTHER INFORMATION: Synthetic
<221> NAME/KEY: misc_feature
<223> OTHER INFORMATION: Residue 1 is modified by a succinyl group.
<221> NAME/KEY: misc_feature
<223> OTHER INFORMATION: Residue 4 is modified by a
     4-methylcoumarin-7-amide group.

<400> SEQUENCE: 32

Leu Leu Val Tyr
1

<210> SEQ ID NO 33
<211> LENGTH: 4
<212> TYPE: PRT
<213> ORGANISM: Artificial Sequence
<220> FEATURE:
<223> OTHER INFORMATION: Synthetic
<221> NAME/KEY: misc_feature
<223> OTHER INFORMATION: Residue 1 is modified by a succinyl group.
<221> NAME/KEY: misc_feature
<223> OTHER INFORMATION: Residue 4 is modified by a p-nitroaniline
```

-continued

```
    group.

<400> SEQUENCE: 33

Ala Ala Pro Phe
```